United States Patent
Sun et al.

(10) Patent No.: US 12,371,339 B2
(45) Date of Patent: Jul. 29, 2025

(54) COPPER NANOCLUSTERS, THYMINE-MODIFIED HYALURONIC ACID AND POLY(COPPER NANOCLUSTERS), METHOD FOR PREPARING THE SAME, AND APPLICATION THEREOF

(71) Applicant: Shenzhen Profound-View Pharma Tech Co., Ltd, Shenzhen (CN)

(72) Inventors: Taolei Sun, Wuhan (CN); Baisong Chang, Wuhan (CN)

(73) Assignee: Shenzhen Profound-View Pharma Tech Co., Ltd, Shenzhen (CN)

( * ) Notice: Subject to any disclaimer, the term of this patent is extended or adjusted under 35 U.S.C. 154(b) by 688 days.

(21) Appl. No.: 17/304,236

(22) Filed: Jun. 16, 2021

(65) Prior Publication Data

US 2021/0354994 A1 Nov. 18, 2021

Related U.S. Application Data

(63) Continuation of application No. PCT/CN2019/071901, filed on Jan. 16, 2019.

(51) Int. Cl.
| | |
|---|---|
| C01G 3/00 | (2006.01) |
| A61K 9/14 | (2006.01) |
| A61K 33/34 | (2006.01) |
| A61K 47/54 | (2017.01) |
| A61K 47/61 | (2017.01) |
| A61K 47/64 | (2017.01) |
| A61K 47/69 | (2017.01) |
| A61P 25/16 | (2006.01) |
| A61P 25/28 | (2006.01) |
| B82Y 5/00 | (2011.01) |
| B82Y 30/00 | (2011.01) |
| B82Y 40/00 | (2011.01) |
| C08L 5/08 | (2006.01) |

(52) U.S. Cl.
CPC .............. *C01G 3/006* (2013.01); *A61K 9/14* (2013.01); *A61K 33/34* (2013.01); *A61K 47/54* (2017.08); *A61K 47/542* (2017.08); *A61K 47/545* (2017.08); *A61K 47/61* (2017.08); *A61K 47/64* (2017.08); *A61K 47/6923* (2017.08); *A61P 25/16* (2018.01); *A61P 25/28* (2018.01); *C08L 5/08* (2013.01); *B82Y 5/00* (2013.01); *B82Y 30/00* (2013.01); *B82Y 40/00* (2013.01); *C01P 2004/04* (2013.01); *C01P 2004/64* (2013.01)

(58) Field of Classification Search
None
See application file for complete search history.

(56) References Cited

U.S. PATENT DOCUMENTS

2011/0003279 A1* 1/2011 Patel ................... G01D 7/005
436/1

FOREIGN PATENT DOCUMENTS

| CN | 105073097 | * | 2/2014 |
| CN | 104458050 | * | 3/2025 |
| KR | 20080093699 | * | 8/2008 |

OTHER PUBLICATIONS

Manna et al. (Layer by layer self assembly of modified hyaluronic acid/chitosan based on hydrogen bonding, Biomacromolecules, Sep. 14, 2009; 10(9): 2632-9). (Year: 2009).*
Dudzik CG, et al. Coordination features and affinity of the $Cu^{2+}$ site in the α-synuclein protein of Parkinson's disease. Biochemistry. 2011; 50: 1771-7.
Giampietro R, et al. The Pivotal Role of Copper in Neurodegeneration: A New Strategy for the Therapy of Neurodegenerative Disorders. Mol. Pharmaceutics 2018; 15: 808-820.
Jin R, et al. Atomically Precise Colloidal Metal Nanoclusters and Nanoparticles: Fundamentals and Opportunities, Chem. Rev., 2016, 116, 10346-10413.
Kozlowski H, et al., Copper, zinc and iron in neurodegenerative diseases (Alzheimer's, Parkinson's and prion diseases). Coordination Chemistry Reviews 2012; 256: 2129-2141.
Liu X, et al. Atomically Precise Copper Nanoclusters and Their Applications, Coord. Chem. Rev., 2018, 359, 112-126.
Manna U, et al. Layer-by-layer self-assembly of modified hyaluronic acid/chitosan based on hydrogen bonding. Biomacromolecules. 2009; 10: 2632-9.
McLeary FA, et al. Dexamethasone Inhibits Copper-Induced Alpha-Synuclein Aggregation by a Metallothionein-Dependent Mechanism. Neurotox Res. 2018; 33:229-238.
Tristan-Lopez L, et al. Copper and Copper Proteins in Parkinson's Disease. Oxidative Medicine and Cellular Longevity. 2014; Article ID 147251.
Yang D, et al. Poly(thymine)-Templated Selective Formation of Copper Nanoparticles for Alkaline Phosphatase Analysis Aides . . . . ACS Appl. Nano Mater. 2018; 1: 168-174.
Yao Q, et al. Toward Total Synthesis of Thiolate-Protected Metal Nanoclusters, Acc. Chem. Res.; 2018; 51; 1338-1348.

* cited by examiner

*Primary Examiner* — Melissa S Mercier
(74) *Attorney, Agent, or Firm* — Yihe Intellectual Property Services Co. Ltd; George Liu

(57) ABSTRACT

Copper nanoclusters (CuNCs), thymine-modified hyaluronic acid (TMHA), and poly(copper nanoclusters) (PCuNCs) are disclosed. In certain embodiments, the TMHA is represented by formula I, wherein the degree of substitution of thymine in the HA is in a range of 1-50%, and wherein n for GlcA-GlcNAc repeats is an integer, from 10 to 10,000.

13 Claims, 21 Drawing Sheets

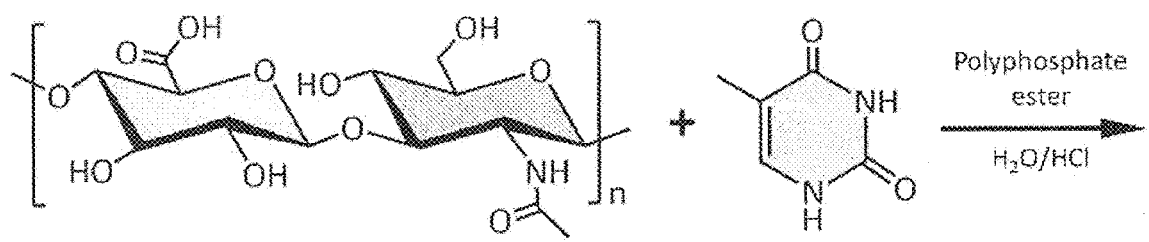
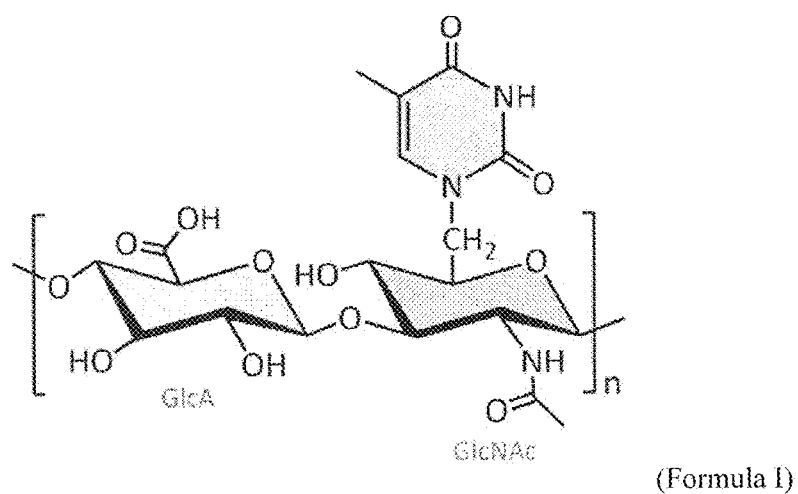
(Formula I)
Fig. 1B
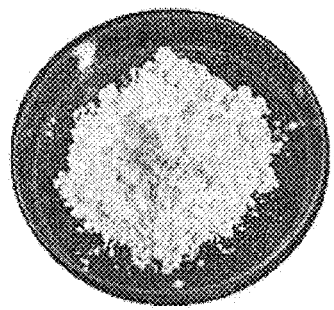 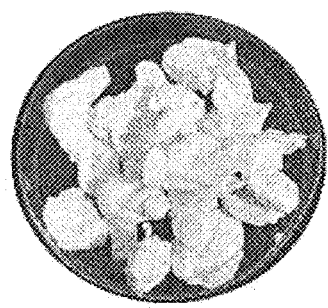
Fig. 1C　　　　　　　　Fig. 1D

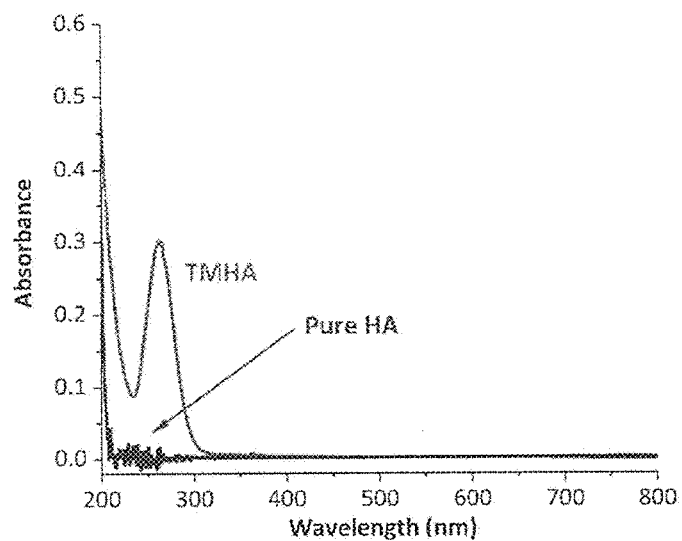
Fig. 1E
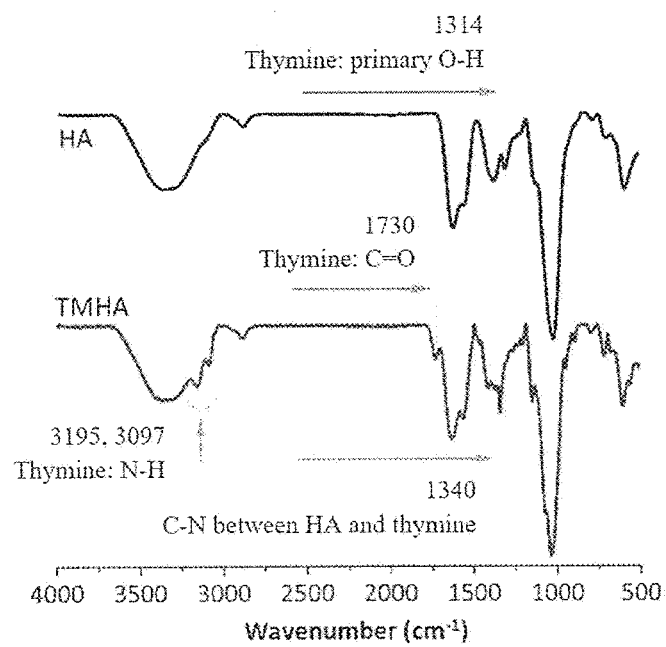
Fig. 1F
Fig. 1 (cont'd)

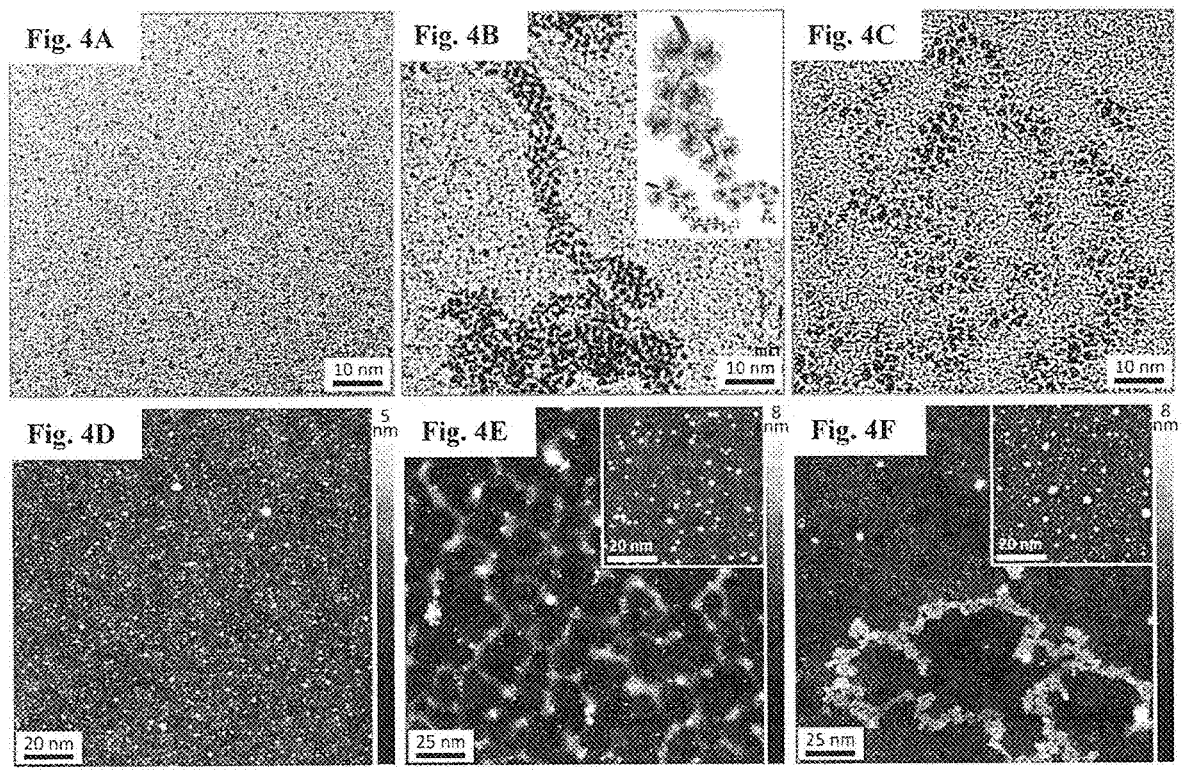

COPPER NANOCLUSTERS, THYMINE-MODIFIED HYALURONIC ACID AND POLY(COPPER NANOCLUSTERS), METHOD FOR PREPARING THE SAME, AND APPLICATION THEREOF

FIELD OF THE INVENTION

The present invention relates to the technical field of nano-drugs, particularly to copper nanoclusters (CuNCs), thymine-modified hyaluronic acid (TMHA), and poly (copper nanoclusters) (PCuNCs), their preparation methods, and their applications in detection, diagnostics, and treatment of for example Parkinson's disease.

BACKGROUND OF THE INVENTION

Neurodegenerative diseases are one of the major threats to human health. Their common pathological features are abnormal entanglement of proteins and their amyloidosis in nerve cells, and associated neuronal apoptosis and neurological impairment. Parkinson's disease (PD) is the second most common neurodegenerative disorder characterized by tremor, muscle rigidity, bradykinesia, postural instability, and movement impairments. PD mainly occurs among old people, and the incidence increases with age. The number of PD patients wordwide, according to a conservative estimation, has exceeded 10 million. However, the etiology of PD is still unknown. In terms of clinical treatment, although several drugs have been approved by the US FDA to treat mild and moderate PD, these drugs only temporarily improve the PD patient's cognitive or motor functions. The symptoms will rebound soon when patients stop taking the medicine. Till now, no drug can terminate or reverse the pathological process of PD. Therefore, it is extremely important to develop new drugs for the treatment of PD.

The main pathological hallmarks of PD are the loss of dopaminergic neurons and the presence of intracellular proteinaceous inclusions, named Lewy bodies, in brainstem, spinal cord, and cortex. The Lewy bodies mainly comprise of amyloid fibers formed by the aggregation of denatured α-synuclein (α-syn). α-syn is located at the presynaptic membrane terminal of neurons. The natural α-syn in cells is highly soluble and natively unfolded. Misfolding of α-syn occurs under pathological conditions, and generates β-sheet structures, which in turn are aggregated and fibrillated to form Lewy body lesions.

Copper is a rare element required for many biological functions in humans. α-syn has a high affinity toward metal ions, such as $Cu^{2+}$. $Cu^{2+}$-α-syn interaction has been implicated in increased oxidative stress and production of toxic oligomers. The toxic oligomers, in vitro, could form porelike structures in the membrane bilayer changing conductance activity and, in vivo, break the membranes leading to cell death. Additionally, copper ions can perform a cooperative binding with dopamine (DA) to α-syn, enhancing the fibrillation of α-syn to a greater extent. Dysregulation of copper homeostasis has been found in PD patients. Recent studies showed a reduced total tissue copper in the substantia nigra (SN); but high levels of unbound copper have been found in the CSF, probably responsible for motor impairments. Elevated levels of $Cu^{2+}$ are associated with PD. Based on the above findings, PD treatment focusing on regulating copper dyshomeostasis in PD has been widely assessed. Preclinical studies in a PD animal model investigated clioquinol, the previously described copper chelator, for its potential use in PD therapy. It has been found that clioquinol increased neuron survival in the SN. Furthermore, the in vivo assessment of the copper ion complex $Cu^{2+}$-diacetylbis(4-methylthiosemicarbazone) ($Cu^{2+}$ (atsm)) in four different PD animal models showed neuroprotection, improvement of cognitive performance, and restoration of motor function (Giampietro R, et al. 2018; Kozlowski H, et al. 2012; Tristan-Lopez L, et al. 2014). In vitro studies also found the formation of $Cu^{2+}$-α-syn complex (Dudzik C G, et al. 2011), and Cu-dependent α-syn intracellular aggregates (McLeary F A, et al. 2018).

Copper nanoclusters (CuNCs) are a kind of substances in between copper atom and copper nanocrystals. The are composed of several to dozens of copper atoms with stabilizing ligands on the surface (Yao Q, et al. 2018). CuNCs have attracted considerable attention owing to their unique size-dependent optical and electronic properties and thus exhibit great potentials in a wide range of applications, e.g. nanocatalysts, biosensors, cellular labeling, and optoelectronic nanodevices (Jin R, et al. 2016; Liu X, et al. 2018). To the best of our knowledge, applying CuNCs into Parkinson's disease treatment has not be reported before. Moreover, using compounds to initiate the in vivo synthesis of CuNCs or poly(copper nanoclusters) (PCuNCs) from endogenous $Cu^{2+}$ has never been published to date in Parkinson's disease treatments.

Manna et al. disclose a stable multilayer film for drug delivery, where the stable multilayer film is constructed based on hydrogen bonding between DNA base (adenine and thymine) pairs substituted on the backbone of chitosan and hyaluronic acid (HA). Chitosan was modified with adenine, whereas HA was modified with thymine. Subsequently, these two polymers were sequentially absorbed on flat substrate by taking advantage of interactions of DNA base pairs via hydrogen bonding. The thymine modified HA in this paper is used in a pairwise manner with adenine modified chitosan as a passive carrier for drug delivery. In order to achieve the required strength of interaction between the thymine modified HA and adenine modified chitosan, high degree of substitution of thymine modified HA is used, e.g. over 75% (Manna U, et al. 2009).

Yang et al. disclose a fluorescent method for the detection of alkaline phosphatase based on poly(thymine)-templated selective formation of copper nanoparticles (CuNPs) and alkyne-azide cycloaddition "click" reaction, where the $Cu^+$ is used as the Cu resources for the synthesis of CuNPs in the presence of ascorbic acid and DNA templates (Yang D, et al. 2018). However, Yang et al. did not disclose the use of thymine as a ligand to form copper nanoclusters.

SUMMARY OF THE INVENTION

The present invention provides copper nanoclusters (CuNCs) modified with one or more ligands.

In certain embodiments of the CuNCs, the ligand-modified CuNCs have a diameter in the range of 0.5-5 nm.

In certain embodiments of the CuNCs, the ligand-modified CuNCs have a diameter in the range of 0.5-3 nm.

In certain embodiments of the CuNCs, the ligand-modified CuNCs have a diameter in the range of 0.5-2.5 nm.

In certain embodiments of the CuNCs, the one or more ligands is (are) selected from the group consisting of thymine, L(D)-cysteine and other cysteine derivatives such as N-isobutyryl-L-cysteine (L-NIBC), N-isobutyryl-D-cysteine (D-NIBC), N-acetyl-L-cysteine and N-acetyl-D-cysteine, cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol and dodecyl mercaptan.

The present invention provides compositions for treating a subject with Parkinson's disease (PD), comprising copper nanoclusters (CuNCs); and a pharmaceutically acceptable excipient.

The present invention provides a use of copper nanoclusters (CuNCs) to manufacture of a medication for treatment of Parkinson's disease (PD).

The present invention provides a process for treating a subject with Parkinson's disease (PD), comprising administering to the subject an effective dosage of a composition comprising copper nanoclusters (CuNCs).

The present invention provides thymine-modified hyaluronic acid (TMHA), wherein the TMHA is represented by formula I:

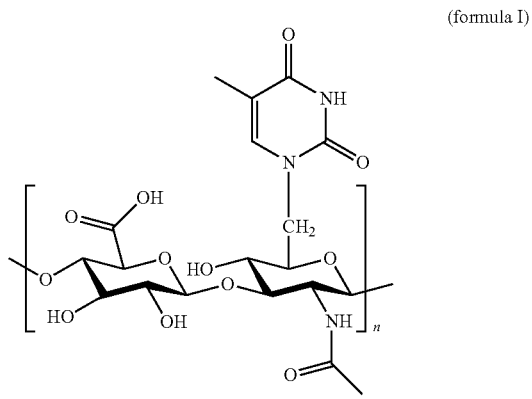

(formula I)

wherein the degree of substitution of thymine in the HA is in a range of 1-50%, and wherein n for GlcA-GlcNAc repeats is an integer, from 10 to 10,000.

In certain embodiments of the TMHA, the degree of substitution of thymine in the HA is in a range of 4-30%.

In certain embodiments of the TMHA, the degree of substitution of thymine in the HA is in a range of 5-20%.

In certain embodiments of the TMHA, the degree of substitution of thymime in the HA is in a range of 7-16%.

In certain embodiments of the TMHA, the degree of substitution of thymine in the HA is in a range of 8-15%.

In certain embodiments of the TMHA, the n is from 10 to 1,000.

In certain embodiments of the TMHA, the n is from 10 to 100.

The present invention provides compositions for treating a subject with Parkinson's disease (PD), comprising thymine-modified hyaluronic acid (TMHA); and a pharmaceutically acceptable excipient.

The present invention provides a use of thymine-modified hyaluronic acid (TMHA) to manufacture of a medication for treatment of Parkinson's disease (PD).

The present invention provides a process for treating a subject with Parkinson's disease (PD), comprising administering to the subject an effective dosage of a composition comprising thymine-modified hyaluronic acid (TMHA).

The present invention provides a kit for detecting Cu ions in a solution, where the kit comprises TMHA; wherein the presence of Cu ions in the solution is indicated by fluorescence at 620 nm detected by fluorescence spectrometer.

In certain embodiments of the kit, the solution is urine or blood.

The present invention provides a method for detecting Cu ions in a solution, comprising mixing the solution with TMHA; incubating for a period of time; and detecting the fluorescence at 620 nm by fluorescence spectrometer.

In certain embodiment of the method, the solution is urine or blood.

The present invention provides poly(copper nanoclusters) (PCuNCs), comprising thymine-modified hyaluronic acid (TMHA); and a plurality of copper nanoclusters (CuNCs); wherein the CuNCs are disposed along the TMHA to form the PCuNCs.

In certain embodiments of the PCuNCs, the molar ratio between Cu and TMHA is 10:1 to 500:1.

In certain embodiments of the PCuNCs, the plurality of CuNCs are with diameters of 0.5-3 nm.

The present invention provides compositions for treating a subject with Parkinson's disease (PD), comprising poly(copper nanoclusters) (PCuNCs); and a pharmaceutically acceptable excipient.

The present invention provides a use of poly(copper nanoclusters) (PCuNCs) to manufacture of a medication for treatment of Parkinson's disease (PD).

The present invention provides a process for treating a subject with Parkinson's disease (PD), comprising administering to the subject an effective dosage of a composition comprising poly(copper nanoclusters) (PCuNCs).

The objectives and advantages of the invention will become apparent from the following detailed description of preferred embodiments thereof in connection with the accompanying drawings.

DESCRIPTION OF THE DRAWINGS

Preferred embodiments according to the present invention will now be described with reference to the Figures, in which like reference numerals denote like elements.

FIG. 1(a)(ii) illustrates the synthesis of TMHA, and FIG. 1(a)(iii) and (iv) show the typical appearance of HA and TMHA respectively.

In FIG. 4, insets: (b, g, h) schematic illustration of PCuNCs nanowires, ionization fragments and PCuNCs, respectively; (e, f) isolated CuNCs that are composed of nanowires.

DETAILED DESCRIPTION OF THE EMBODIMENTS

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The present invention provides thymine-modified hyaluronic acid (TMHA) and a process of synthesizing TMHA.

Figure 1A:
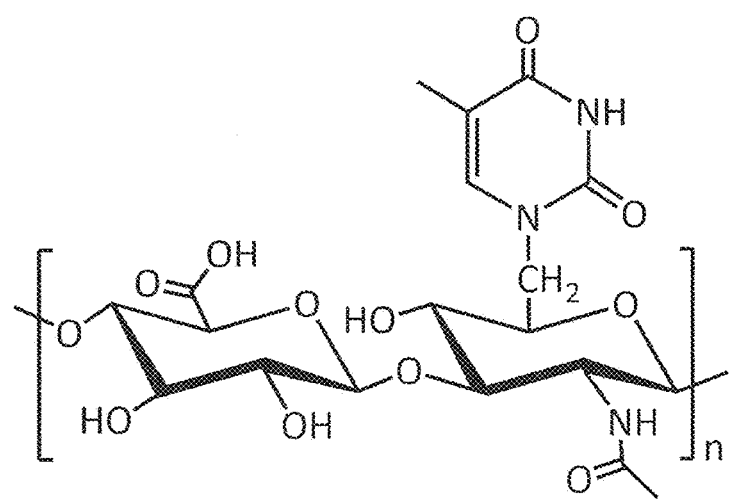
FIG. 1(a)(i) shows the structure of TMHA represented by Formula 1.

The structure of TMHA is represented by Formula 1 as shown in FIG. 1(a) (i), where the HA is composed of glucuronic acid (GlcA)-N-acetylglucosamine (GlcNAc) repeats, the GlcNAc is modified by thymine, and n is an integer, from 10-10,000, preferably 10-1,000, more preferably 10-100. It is to be noted that not every single GlcNAc in the HA is modified by a thymine. The degree of substitution (DS) of thymine in TMHA is defined as the number of thymine moledules per 100 sugar residues of TMHA. The degree of substitution (DS) of thymine in TMHA is in the range of 1-50%, further to 4-30%, yet further to 5-20%, yet further to 7-16%, and yet further to 8-15%.

The process of synthesizing TMHA comprises:
providing an acidic aqueous solution of thymine in a concentration of 0.05-0.02 w/v %; in certain embodiments, the acidic aqueous solution is composed of water and HCl;
providing an HA solution in a concentration of 1-5 wt %;
adding a catalyst into the HA solution; in certain embodiments, the catalyst is polyphosphate ester;
adding the acidic aqueous solution of thymine into the catalyst-containing HA solution to form an HA-thymine mixture; in certain embodiments, the acidic aqueous solution of thymine is added by dropwise injection;
heating the HA-thymine mixture for a predetermined period; in certain embodiments, the heating is at 45-50° C. for a period of 12-20 hours in an oil-bath;
cooling the heated HA-thymine mixture to a predetermine temperature; in certain embodiments, the predetermined temperature is about 0° C. to precipitate unreacted thymine;
dialyzing supernatant solution from the cooled HA-thymine mixture; in certain embodiments, the dialysis is performed for 48-96 hours with molecular weight cut off 8000 to remove the unreacted reagents and impurities; and
lyophilizing the dialyzed solution to obtain TMHA.

The present invention also provides poly(copper nanoclusters) (PCuNCs) and a process of synthesis of PCuNCs.

In certain embodiments, the process of PCuNCs synthesis comprises:
providing a TMHA solution; in certain embodiments, the TMHA solution is 0.1 mM, pH7.0;
adding $CuSO_4$ solution into the TMHA solution; in certain embodiments, the $CuSO_4$ solution is 20 mM, pH7.0, and were added dropwise;
thereby allowing the mixture to react; in certain embodiments, the reaction is for 20 minutes in dark at 37° C. to obtain the PCuNCs solution; the PCuNCs solution is stored in dark at 4° C. for use.

Under radiation of UV-light (365 nm), a bright orange-red emission is clearly visible, indicating successful formation of luminescent CuNCs.

In certain embodiments, the molar ratio between Cu and TMHA is in the range of 10:1 to 500:1, further in the range of 15:1 to 300:1, yet further in the range of 20:1 to 200:1, yet further in the range of 25:1 to 100:1, and yet further in the range of 30:1 to 80:1.

The PCuNCs contains well dispersed spherical nanoclusters with diameters of 0.5-3 nm.

The present invention provides the use of TMHA to detect Cu ions in a solution. In certain embodiments, the solution is a biological fluid such as urine or blood. In certain embodiment, the detection is performed by mixing a solution with TMHA, incubating for a period of time, and detecting the fluorescence at 620 nm by fluorescence spectrometer.

The present invention provides a composition for treating a subject with Parkinson's disease (PD). In certain embodiments, the composition comprises copper nanoclusters (CuNCs), and a pharmaceutically acceptable excipient.

In certain embodiments, the composition comprises thymine-modified hyaluronic acid (TMHA), and a pharmaceutically acceptable excipient.

In certain embodiments, the composition comprises poly (copper nanoclusters) (PCuNCs), and a pharmaceutically acceptable excipient.

The present invention provides use of copper nanoclusters (CuNCs) to manufacture a medication for treatment of PD.

The present invention provides use of thymine-modified hyaluronic acid (TMHA) to manufacture a medication for treatment of PD.

The present invention provides use of poly(copper nanoclusters) (PCuNCs) to manufacture a medication for treatment of PD.

The present invention provides a process for treating a subject with PD.

In certain embodiments, the process comprises: administering to the subject an effective dosage of a composition comprising copper nanoclusters (CuNCs).

In certain embodiments, the process comprises: administering to the subject an effective dosage of a composition comprising thymine-modified hyaluronic acid (TMHA).

In certain embodiments, the process comprises: administering to the subject an effective dosage of a composition comprising poly(copper nanoclusters) (PCuNCs).

In certain embodiments, the subjects with PD are administered an effective amount of TMHA or PCuNCs by intraperitoneal injection. In certain embodiments, the effective amounts are in the range of 2-100 mg kg$^{-1}$.

The present invention provides copper nanoclusters (CuNCs) modified with one or more ligands. In certain embodiments, the ligand-modified CuNCs have a diameter in the range of 0.5-5 nm, preferably in the range of 0.5-3 nm, and more preferably in the range of 0.5-2.5 nm. In certain embodiments, the ligands include, but not limited to, thymine, L(D)-cysteine and other cysteine derivatives such as N-isobutyryl-L-cysteine (L-NIBC), N-isobutyryl-D-cysteine (D-NIBC), N-acetyl-L-cysteine and N-acetyl-D-cysteine, cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol and dodecyl mercaptan.

The following examples are provided for the sole purpose of illustrating the principles of the present invention; they are by no means intended to limit the scope of the present invention.

EXAMPLES

(1) Synthesis of Thymine Modified Hyaluronic Acid (TMHA)

First, polyphosphate ester as a catalyst was prepared. Diethyl ether (14.5 mL) and CHCl$_3$ (5.6 mL) were added to phosphorus pentoxide (10 g) with stirring, and the mixture was heated under reflux for 12 h at 50° C. to obtain a clear solution. After cooling down to room temperature, the solvent was distilled off under vacuum. The resultant colorless viscous residue was polyphosphate ester and used as a catalyst without further purification.

Second, the TMHA was synthesized as follows. A clear solution of thymine (23.6 mg) was obtained by dissolving in 25 mL of H$_2$O with the addition of 0.25 mL of concentrated HCl solution (25%). Polyphosphate ester (1.5 g) was added to HA solution (50 mL, 2.2 wt %; MW120KD), followed by dropwise injection of thymine, and the mixture was heated to 50° C. for 16 h in an oil-bath and cooled down to 0° C. to precipitate unreacted thymine. Then, the supernatant solution was dialyzed for 72 h via a dialysis bag (molecular weight cut off 8000) to remove any unreacted reagents and impurities. The resultant solution was lyophilized to obtain TMHA; the yield was 86%, and the degree of substitution (DS) was 10.5%. The quality of final product was characterized by 1H NMR and FT-IR.

Figures 1, 1G:
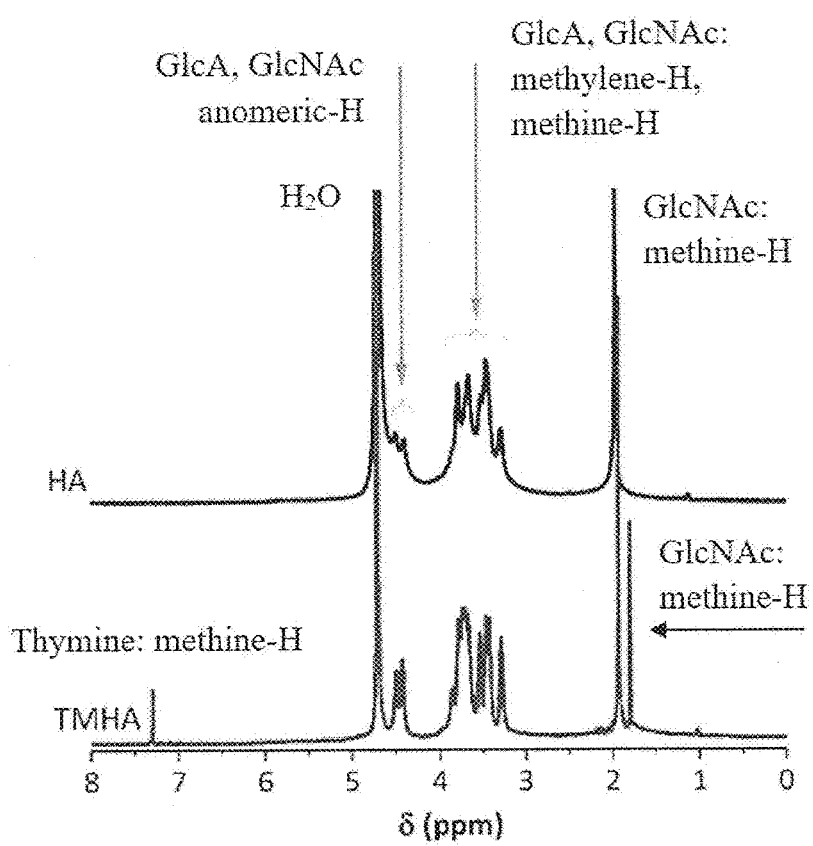
FIG. 1(b) shows UV-vis spectra of TMHA (red line) and pure HA (blue line), respectively.
FIG. 1(c) shows FT-IR of HA and TMHA.
FIG. 1(d) shows $^1$H NMR spectra of HA and TMHA.
Figure 2A:
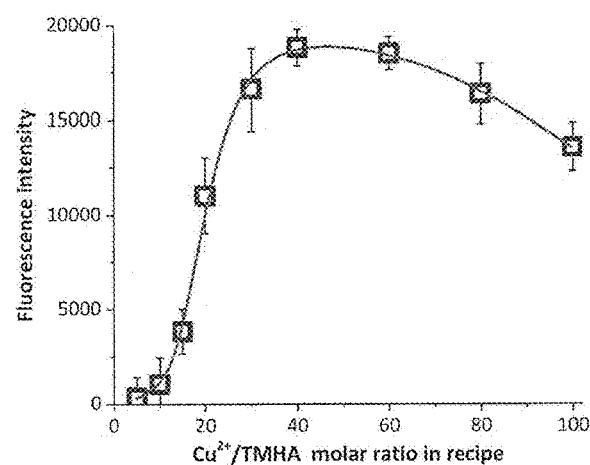
FIG. 2 provides graphs showing the effects of (a) molar ratios between $Cu^{2+}$ and TMHA, (b) reaction pH values, (c) reaction temperature, and (d) reaction time on the photoluminescence intensity of the resultant PCuNCs.
Figure 2B:
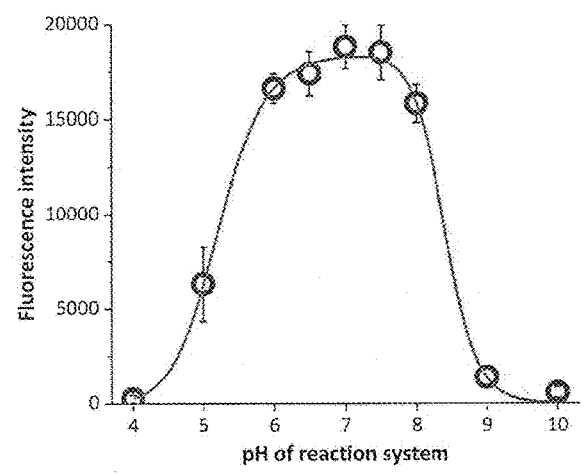
Figure 2C:
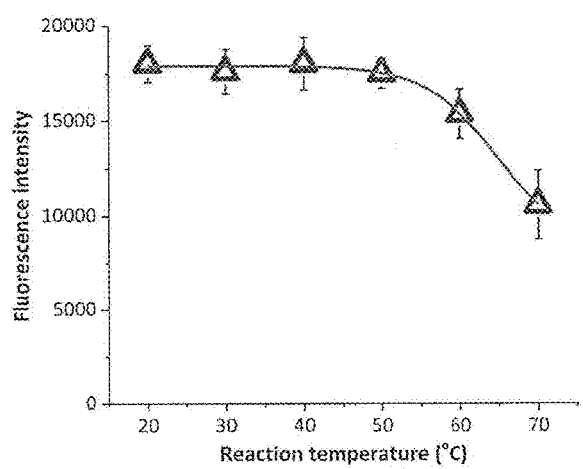
Figure 2D:
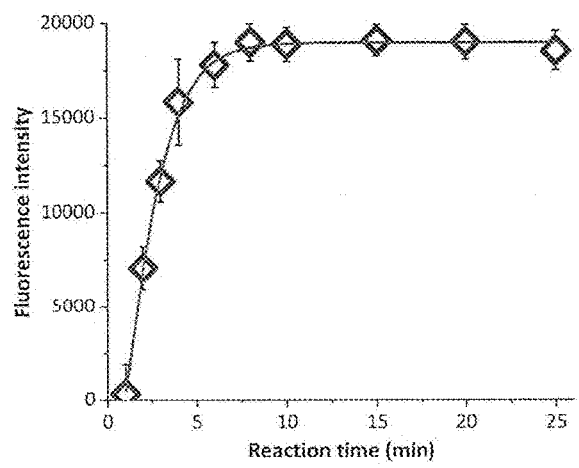
Figure 3A:
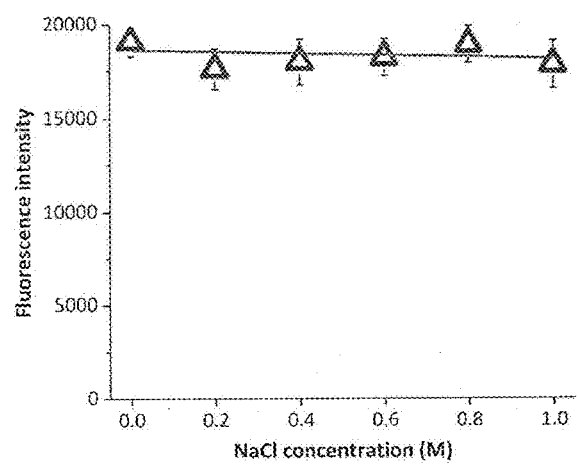
FIG. 3 provides graphs showing the effects of (a) NaCl concentrations (0-1 M), (b) common cations and anions, (c) pH values (4-10), and (d) storage time (0-5 weeks) on the fluorescence intensity of as-obtained PCuNCs.
Figure 3B:
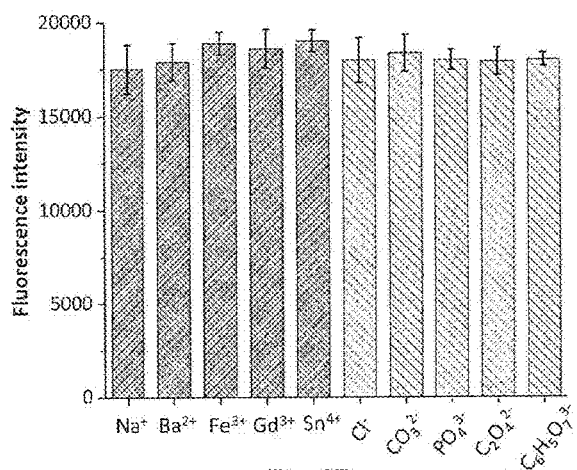
Figure 3C:
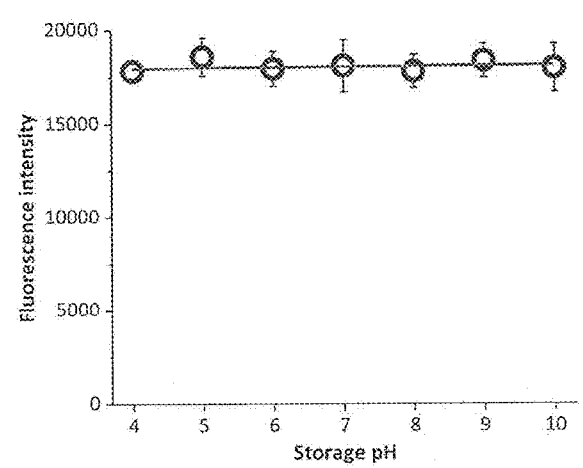
Figure 3D:
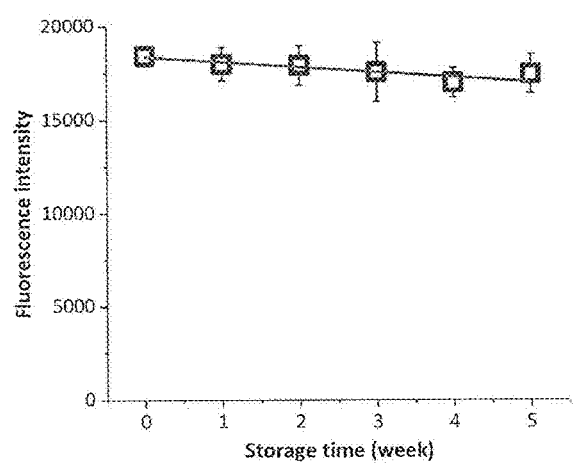

Referring now to FIG. 1, FIG. 1(a)(ii) illustrates the synthesis of TMHA, and FIG. 1(a)(iii) and (iv) show the typical appearance of HA and TMHA respectively; FIG. 1(b) shows UV-vis spectra of TMHA (red line) and pure HA (blue line), respectively; FIG. 1(c) shows FT-IR of HA and TMHA; and FIG. 1(d) shows 1H NMR spectra of HA and TMHA. The $^1$H NMR spectra were carried out in D$_2$O at 80° C. and 400 MHz at a sample concentration of 10 mg mL$^{-1}$. For FTIR analysis, KBr crystals were used as the matrix during sample preparation.

The chemical structure of TMHA conjugate was qualitatively studied by FTIR in virtue of comparing the spectra of native HA and those of its derivatives. These spectra displayed significant differences in the range of 3000-3200 cm$^{-1}$ and 1300-1800 cm$^{-1}$ compared to that of the native HA, especially to the TMHA derivatives with higher DS. Characteristic peaks assignments of the native HA were 3360 cm$^{-1}$ (secondary O—H stretch), 2873 cm$^{-1}$ (C—H stretch), 1622 cm$^{-1}$ (amide II band, C—O stretch of acetyl group), 1554 cm$^{-1}$ (amide II band, N—H stretch), 1380 cm$^{-1}$ (asymmetric C—H stretch bending of CH2 group), 1314 cm$^{-1}$ (O—H stretch of primary alcoholic group), and 1026 cm$^{-1}$ (skeletal vibration involving the bridge C—O stretch). The spectrum of TMHA derivatives displayed three characteristic peaks, i.e., 3195 and 3079 cm$^{-1}$ (N—H stretch), 1730 cm$^{-1}$ (C=O stretch), and 1340 cm$^{-1}$ (C—N stretching vibration), hinting the functionalization of HA by thymine. More importantly, the disappearance of a band at 1314 cm$^{-1}$, which was ascribed to the O—H stretch of primary alcoholic group belonging to HA, suggested the reaction mechanism that only the primary-OH group of GlcNAc of HA reacted with thymine. The successful modification was further confirmed by 1H NMR analysis.

(2) Synthesis of Poly(Copper Nanoclusters) (PCuNCs) with TMHA 10 mL of TMHA (DS of 10.5%) solution (0.1 mM, pH 7.0) was gradually heated up to 37° C. to dissolve the TMHA. 2 mL of $CuSO_4$ (20 mM, pH 7.0) solution was added dropwise and allowed to react for another 20 min in dark at 37° C. Under radiation of UV-light (365 nm), a bright orange-red emission was clearly visible, indicating the successful formation of luminescent PCuNCs. Finally, the resultant solution was stored in dark at 4° C. for use.

The optimal synthesis conditions, e.g., molar ratio of $Cu^{2+}$/TMHA, pH value, reaction temperature, and time were studied in detail respectively. To investigate the effect of $Cu^{2+}$ content in reaction system, 2 mL of $CuSO_4$ with varied concentrations was added into 10 mL of TMHA solution, in which the molar ratio of $Cu^{2+}$ to TMHA in this reaction system was from 5:1, 10:1, 15:1, 20:1, 30:1, 40:1, 60:1, 80:1, to 100:1. After reacted with gentle stirring in the dark at 37° C. and pH 7.0 for 20 min, the colloidal samples were obtained and tested by luminescence spectrophotometer. To better understand the influence of pH values on the formation of PCuNCs, a series of experiments were carried out at different pH adjusting by 1.0 M NaOH or 1.0 M HCl under otherwise identical environments. Also, the effects of reaction temperature (20-70° C.), and reaction time (1-25 min) were studied respectively. The resultant samples were tested by luminescence spectrophotometer.

Referring now to FIG. 2, there are provided graphs showing the effects of (a) molar ratios between $Cu^{2+}$ and TMHA, (b) reaction pH values, (c) reaction temperature, and (d) reaction time on the photoluminescence intensity of the resultant PCuNCs. As shown in FIG. 2(a), the fluorescence intensity of PCuNCs was enhanced with molar ratios between $Cu^{2+}$ and TMHA increasing from 5 to 40, and gradually declined with further increasing $Cu^{2+}$/TMHA ratio from 40 to 100. As shown in FIG. 2(b), the reaction pH values played an important role in the formation of high-quality PCuNCs. The fluorescence intensity of the PCuNCs greatly climbed up with the reaction pH values increasing from 4 to 7, and then began to decline rapidly. For instance, at reaction pH 10, the emission of PCuNCs could be hardly monitored via the fluorescence spectroscopy. As shown in FIG. 2(c), the reaction temperature ranging from 20 to 50° C. was the ideal parameter in the formation of highly fluorescent PCuNCs. As shown in FIG. 2(d), the fluorescence intensity of prepared PCuNCs significantly improved as the synthetic time was prolonged from 1 min to 8 min. When the time was continually increased to 25 min, the fluorescence intensity of PCuNCs kept constant. Based on all the observations, it was confirmed that the highest fluorescence intensity of the PCuNCs can be obtained at the following optimized synthetic conditions: $Cu^{2+}$ and TMHA with the molar ratio of about 40 in a pH 7.0 solution, and then reacting at 37° C. for 4 h.

(3) Investigation of the Stability of PCuNCs

The evaluation of luminescent stability of PCuNCs was conducted according to the following procedures. First, various concentrations of NaCl solution (100 μL) were mixed with PCuNCs solution (900 μL) and incubated at 25° C. for 30 min. Second, 500 μL solution of PCuNCs and various positive or negative ion solutions (500 μL, 2 mM) were mixed thoroughly and incubated at 25° C. for 30 min. Third, NaOH (1.0 M) or HCl (1.0 M) was introduced into 5 mL of PCuNCs solution to adjust the system pH and incubated at 25° C. for 30 min. Finally, fluorescent spectra of PCuNCs were measured at an excitation wavelength at 385 nm and emission wavelength at 610 nm.

Referring now to FIG. 3, there are provided graphs showing the effects of (a) NaCl concentrations (0-1 M), (b) common cations and anions, (c) pH values (4-10), and (d) storage time (0-5 weeks) on the fluorescence intensity of as-obtained PCuNCs. As shown in FIG. 3(a), the fluorescence intensity of PCuNCs remained unchanged in the presence of NaCl solution with different concentrations (0, 0.2, 0.4, 0.6, 0.8 and 1.0 M), demonstrating a good stability of PCuNCs in a strong ionic strength environment. More importantly, upon addition of 2 mM of other traditional metal ions, such as $Na^+$, $Ba^{2+}$, $Fe^{3+}$, $Gd^{3+}$, $Sn^{4+}$ and anions, such as $Cl^-$, $CO_3^{2-}$, $PO_4^{3-}$, $C_2O_4^{2-}$, $C_6H_5O_7^{3-}$, to the solution of PCuNCs, it was found that all these selected ions manifested negligible interferences on the fluorescence intensity (FIG. 3(b)). A similar stable fluorescence performance was also recorded displayed in FIG. 3(c). Adjusting the pH values from 4.0 to 10.0 did not evidentially influence the corresponding fluorescence spectra of PCuNCs. It obviously demonstrated that the PCuNCs were insensitive to the pH values in the present buffer system. Moreover, after storage for 5 weeks in air at room temperature (25° C.), no precipitates, flocculation, or decline of fluorescence intensity was observed for PCuNCs (FIG. 3(d)). All these results together suggested the outstanding stability of PCuNCs, making them very promising for practical applications.

(4) The Effect of the Degree of Substitution (DS) of Thymine in TMHA on the Synthesis of PCuNCs Hyaluronic acid (HA) and thymine are two natural biomolecules; thymine responsible for efficiently chelating $Cu^{2+}$, and hydroxyl group of HA as the reducing agent for nucleation and growth of metal nanoclusters. The inventors of the present invention discovered that the degree of substitution (DS) of thymine was a key regulatory factor in the synthesis of PCuNCs. $Cu^{2+}$ and TMHA with the molar ratio of about 50 in a pH 7.0 solution, and then reacting at 37° C. for 4 h.

Figure 4I:
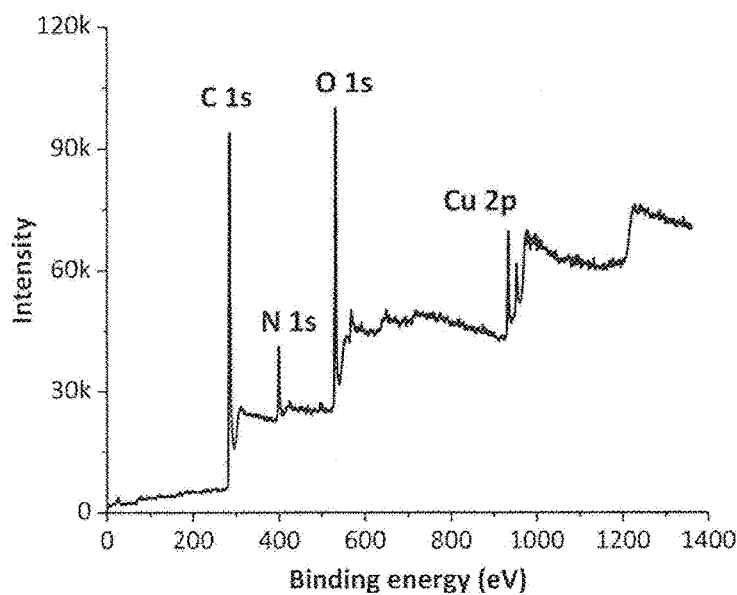
FIGS. 4(i) and (j) show XPS spectra of (i) full region of CuNCs and (j) Cu 2p region.
Figure 4J:
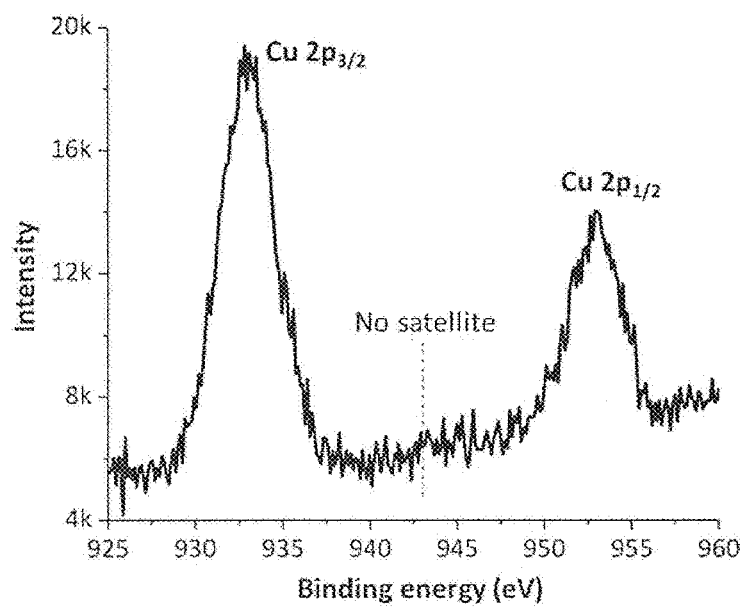
FIG. 4 provides photographs and graphs showing PCuNCs prepared with TMHAs with different degree of substitutions (DS) of thymine.
FIGS. 4(a) and (d) show the TEM or AFM images of PCuNCs prepared by TMHA with 3.2% DS of thymine respectively.
FIGS. 4(b) and (e) show the TEM or AFM images of PCuNCs prepared by TMHA with 10.5% DS of thymine respectively.
FIGS. 4(c) and (f) show the TEM or AFM images of PCuNCs prepared by TMHA with 20.1% DS of thymine respectively.
FIGS. 4(g) and (h) show the MS spectra of TMHA or PCuNCs respectively.

Referring now to FIG. 4, there are provided photographs and graphs showing PCuNCs prepared with TMHAs with different degree of substitutions (DS) of thymine. FIGS. 4(a) and (d) show the TEM or AFM images of PCuNCs prepared by TMHA with 3.2% DS of thymine respectively; FIGS. 4(b) and (e) show the TEM or AFM images of PCuNCs prepared by TMHA with 10.5% DS of thymine respectively; FIGS. 4(c) and (f) show the TEM or AFM images of PCuNCs prepared by TMHA with 20.1% DS of thymine respectively; FIGS. 4(g) and (h) show the MS spectra of TMHA or PCuNCs respectively; and FIGS. 4(i) and (j) show XPS spectra of (i) full region of CuNCs and (j) Cu 2p region. In FIG. 4, insets: (b, g, h) schematic illustration of PCuNCs nanowires, ionization fragments and PCuNCs, respectively; (e, f) isolated CuNCs that are composed of nanowires.

The DS of thymine at the level of 10.5% generated well-dispersed spherical CuNCs with diameters in a range of 0.5~3 nm, the average diameters of which are 1.64±0.48 nm. In contrast, at either a low (3.2%) or high (20.1%) level, abundant fluffy CuNCs were present with diameters of 1.08±0.72 nm and 1.96±0.83 nm, respectively. Subsequently replacing TMHA with blank HA under otherwise identical experiment factors only showed severely fused macromolecular networks (FIGS. 4(i) and (j)). More surprisingly, the DS of 10.5% yielded one-dimensional assembly of PCuNCs nanowire with diameters of 8.05±0.43 nm (FIGS. 4(b) and (e)). As the DS of thymine was increased to 20.1%, the nanowires were partly blurred in terms of seriously decayed length/diameter ratios (FIGS. 4(c) and (f)). A fine-tuning covalent bond between CuNCs and linear TMHA templates guaranteed that the CuNCs are self-assembled into highly ordered arrays, i.e. PCuNcs. We highlighted that such nanowires efficiently improved PCuNCs' fluorescence stability and intensity (seen below) based on aggregation induced emission (AIE).

(5) Replacement of Thymine with Other Ligands

Figure 5:
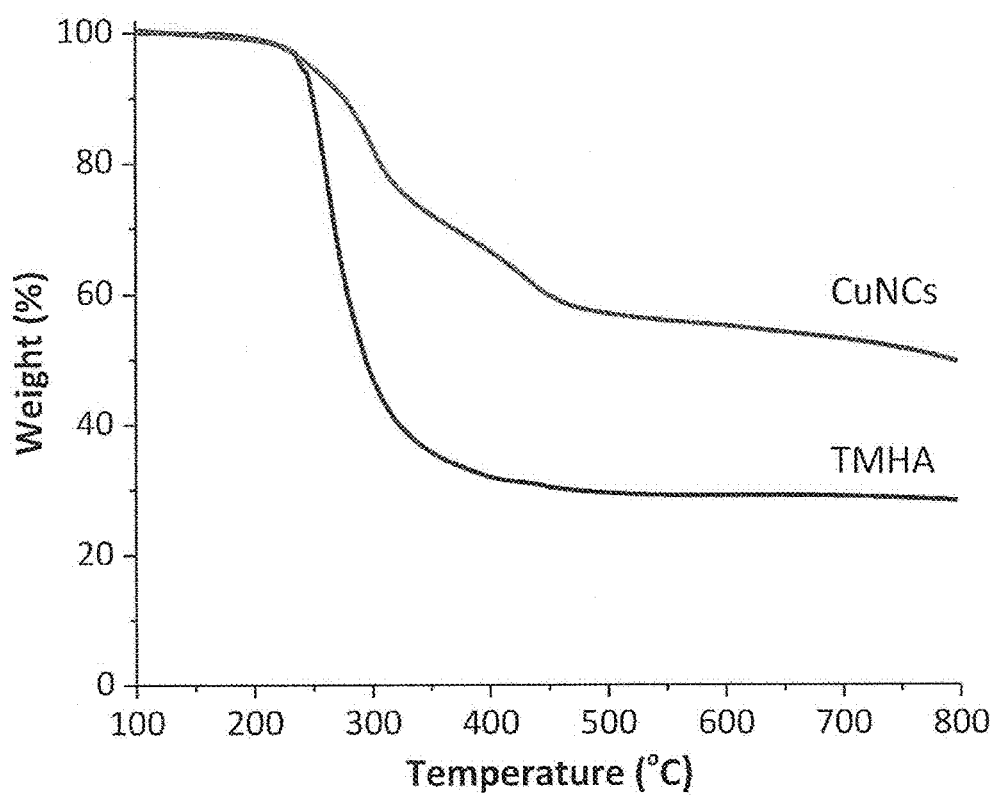
FIG. 5 is a graph showing thermogravimetric analysis of CuNCs with GSH ligand.

To more clearly detect individual CuNCs that form the nanowire, without varying core size of metal, the thymine ligand was replaced with thiolate by creating stronger Cu—S bonds. While GSH as a ligand formed CuNCs as expected, its use facilely disintegrates parent nanowire into its building units, i.e. CuNCs. As shown in FIG. 5, there is a graph showing thermogravimetric analysis of CuNCs with GSH ligand. Here, the strategy of ligand exchange was employed to disintegrate parent nanowire into its building blocks, for example CuNCs. The as-prepared TMHA-templated CuNCs (1 mL) was added to GSH aqueous solution (0.05 M, 5 mL) and kept for stirring for 8 h at room temperature. A white precipitation will be produced as the reaction processed. The resulting supernate was collected by centrifugation at 8000 rpm for about 10 min. The GSH-stabilized CuNCs were precipitated from the supernate by addition of ethanol and washed with ethanol repeatedly for three times. Finally, the product was freeze-dried and stored in the refrigerator for long-term preservation.

(6) Characterization of Pcuncs

Figure 6:
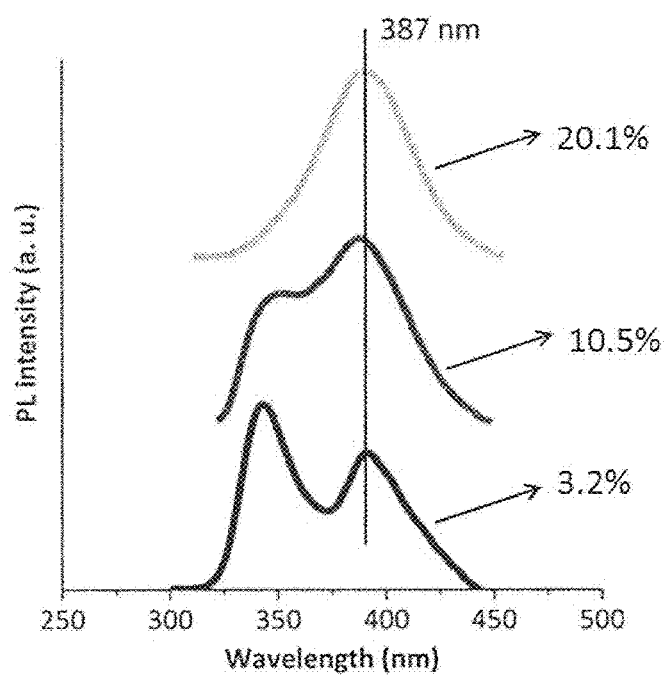
FIG. 6 is a graph showing excitation (measured at 2 cm=613 nm) spectra of CuNCs obtained using the DS of thymine at 3.2% (blue), 10.5% (red), and 20.1 (green), respectively.

Of note, the intermediate DS at 10.5% led to intact, spherical, and uniform CuNCs, corroborating via section profile analysis and polydispersity index. Upon careful calculation from HR-TEM image, inter-fringe spacing of 0.207 nm was found, which matched well with (111) crystal plane of face-centered metallic Cu. FIG. 6 is a graph showing excitation (measured at $\lambda_{em}$=613 nm) spectra of CuNCs obtained using the DS of thymine at 3.2%, 10.5%, and 20.1, respectively.

In the following sections, PCuNCs prepared by TMHA at DS of 10.5% was deliberately used unless otherwise noted.

As a supplement to electron microscope, mass spectrometry (MS) has also been proved to be a reliable tool in cluster size analysis. Here we attempted to utilize high-resolution electrospray ionization MS (ESI-MS) to identify the precise molecular formula of subnanometer-sized CuNCs. Notably, the pure HA gave no any visible ion signals, mainly due to its low ionization efficiency in positive ion mode. The positive ionization of TMHA, in contrast, produced a single peak at m/z=106.1936 (FIG. 4(g)). It can be ascribed to a formula of $[C_4H_5NO+Na]^+$ owing to the loss of HNCO from thymine. $C_4H_5NO$ instead of THMA acting as a ligand in ionization of CuNCs contributed to release abundant ion signals after screening several measurement parameters. Those parameters delivering the appropriate energy to facilitate the decomposition of thymine and, thus chosen as optimal, were capillary voltage of ca. 4500 V and dry temperature of 150° C. By combining element analysis and the highest ion peak at m/z=1043.2545 (FIG. 4(h)), the definitive formula of CuNCs was determined as $Cu_6L_5$. Other ion peaks in a low mass range also corresponded precisely with fragments of $Cu_6$-involved species. As a result, the $Cu_6$ clusters were the dominant species, suggesting superior monodispersity of CuNCs synthesized by TMHA with DS of thymine at 10.5% relative to two controls with the DS at 3.2% and 20.1%.

X-ray photoelectron spectroscopy (XPS) analysis revealed that CuNCs were made up of all the anticipated elements, including C, O, N, and Cu. The inorganic content in CuNCs was calculated to be 29.8 wt %. Moreover, two intense signals at 932.3 and 952.1 eV were assigned to binding energies of $2p_{3/2}$ and $2p_{1/2}$ electrons of $Cu^0$, and no satellite signals implied the lack of $Cu^{2+}$. It was worthwhile mentioning that $2p_{3/2}$ binding energy of $Cu^0$ was very close to that of $Cu^+$. Therefore, the valence states of as prepared CuNCs most likely lied between 0 and +1.

Figure 7:
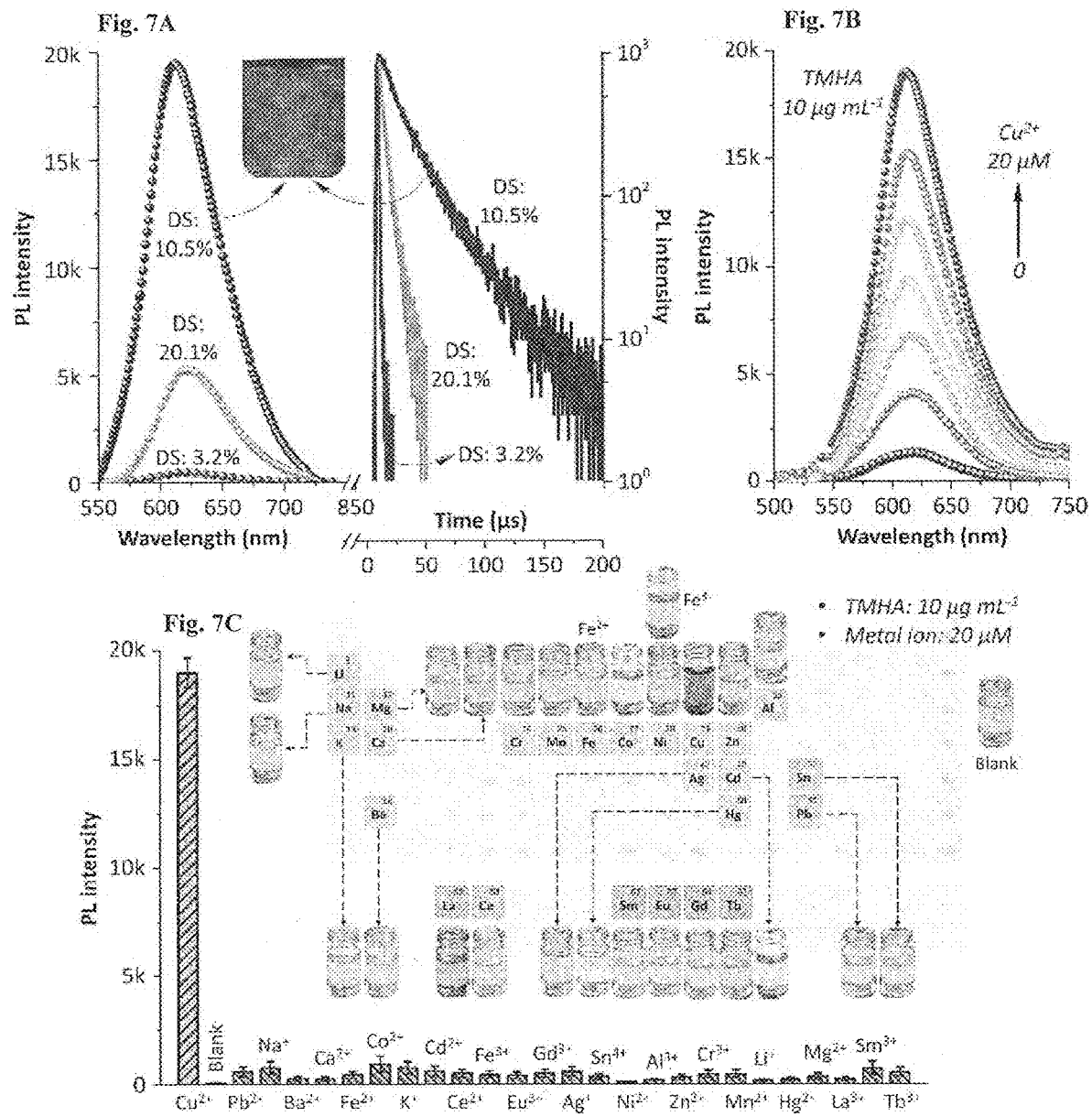
FIG. 7 provides graphs showing: (a) PL spectra (Left) and decay profiles (right) with different DS of thymine. Inset: image with 365 nm excitation. (b) PL response of TMHA probe versus $Cu^{2+}$ content. (c) PL and color change (inset) of TMHA probe for $Cu^{2+}$ against various metals.

Referring now to FIG. 7, there are provided graphs showing: (a) PL spectra (Left) and decay profiles (right) with different DS of thymine. Inset: image with 365 nm excitation. (b) PL response of TMHA probe versus $Cu^{2+}$ content. (c) PL and color change (inset) of TMHA probe for $Cu^{2+}$ against various metals.

(7) TMHA as a Probe for Detection of $Cu^{2+}$ Ions

Five urine samples, in which three of them were collected from healthy adult volunteers and the rest collected from adult volunteers with PD, were diluted by acetonitrile for removing the interference of protein and other biospecies in urine, respectively. After centrifugation with a speed of 12,000 rpm for 10 min at 10° C., the supernatant solution was collected for the following experiments. First, the supernatant was diluted by deionized water in order to decrease the $Cu^{2+}$ concentrations remaining in the supernatant. Then, 100 μL urine sample was mixed with 200 μL of TMHA (0-40 μg mL$^{-1}$), and incubated for 10 min at 25° C. before it was examined by fluorescence spectrometer.

It is worthy to note that, optical feature was clearly different from the surface plasmon resonance of large Cu nanoparticle at 560 nm. The broadening of XRD peaks into a baseline was consistent with tiny size of CuNCs. Interestingly, the subnanoscaled CuNCs possessed DS-dependent photoluminescence (PL) features. Under excitation of 385 nm, 10.5% DS-induced nanowires gave a bright and stable red emission peaked at 613 nm, a long lifetime of 57 μs, and large quantum yield of 14.8% (FIG. 7(a)). These properties faded rapidly for those of less ordered CuNCs assemblies, hinting the self-assembly driven AIE. The more CuNCs packing tightly and orderly, the more stable and intense PL responses. By tuning reaction factors, our clean synthesis route relied on TMHA (chelating, reducing $Cu^{2+}$ and templating self-assembly into CuNC nanowire), eliminating impurities that traditional routes introduced, and affording striking PL properties. For example, the PL intensity of TMHA sensor was linearly and clearly improved in response to $Cu^{2+}$ concentrations (FIG. 7(b)), corresponding to an extremely low detection limit of 2.2 ppb. Compared with currently reported methods, this analytical performance showed about 1.5 and 480 times smaller than state-of-the-art probes and maximal levels of drinking water set by U.S. EPA, respectively. Also, the optical property was selective toward $Cu^{2+}$ relative to foreign ions in FIG. 7(c). Taken together, TMHA can be used as colorimetric and fluorometric $Cu^{2+}$ probe with high sensitivity and selectivity.

(8) Antioxidant Function of CuNCs

The capability of CuNCs to functionally mimic cellular antioxidant enzymes was studied. Strikingly, CuNCs could violently decompose $H_2O_2$ based on a first-order reaction kinetics (FIG. 8(a)). We then studied the GPx-like activity of CuNCs via the nitroblue tetrazolium (NBT) assay. The initial rates recorded at various assay conditions were displayed in FIG. 8(b), which directly supported the GPx-like function of CuNCs. In addition, CuNCs had a remarkable SOD-like activity and the production of mass $O_2$ from $KO_2$ as a superoxide source deduced the working principle: disproportionation of superoxide to $H_2O_2$ and $O_2$ (FIG. 8(c)). Moreover, CuNCs had obvious multienzyme advantages over preexisting metals that are used as cellular antioxidants (FIG. 8(d)).

Figure 8:
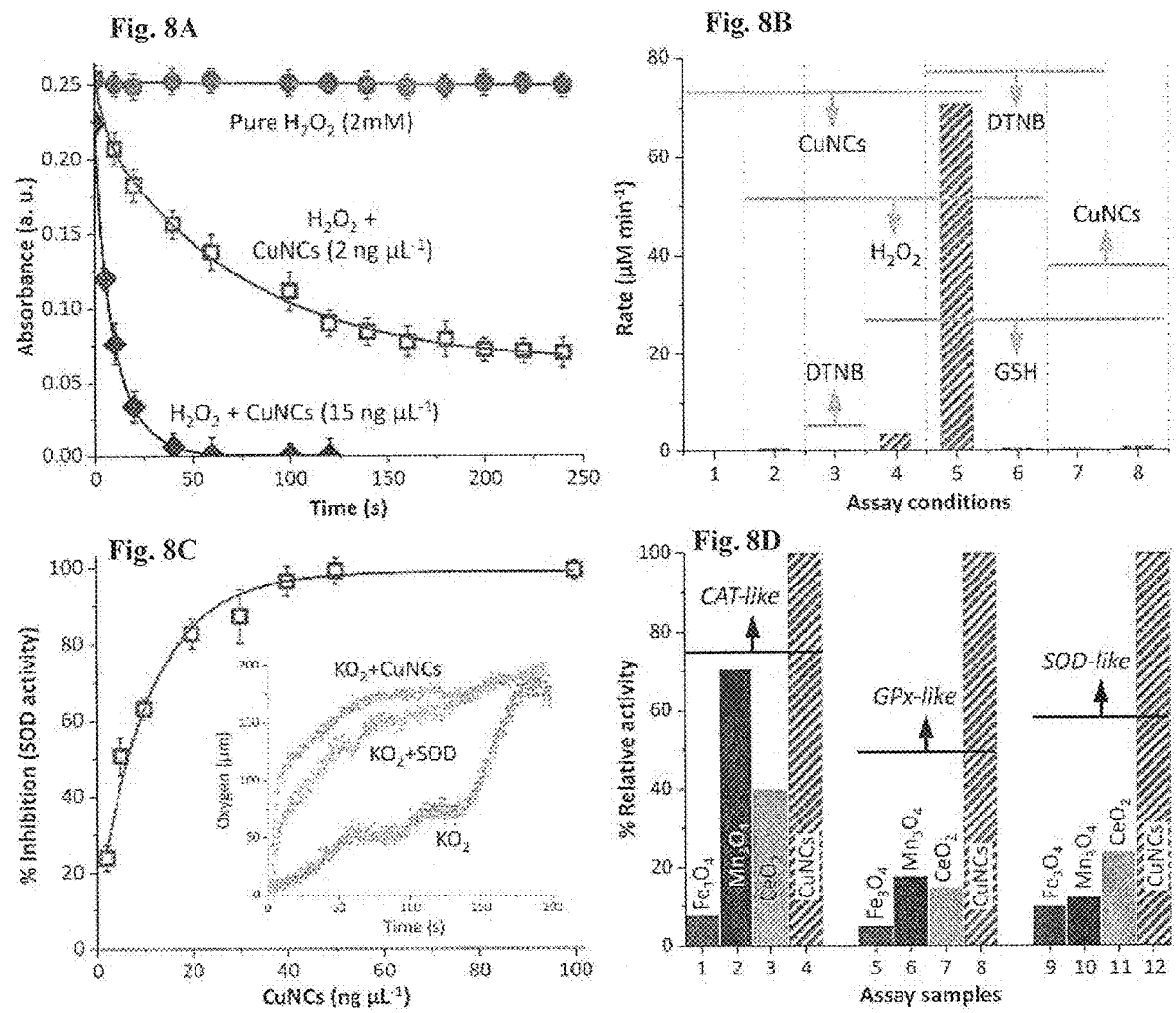
FIG. 8 provides graphs showing: (a) UV absorption of $H_2O_2$ reacting with CuNCs. (b) Initial rates of GPx-like activities of CuNCs and various controls. (c) SOD-like activities of CuNCs. Inset: $O_2$ generation rate. (d) Comparison of catalytic activity of CuNCs with other metals.

Referring now to FIG. 8, there are provided graphs showing: (a) UV absorbance of $H_2O_2$ reacting with CuNCs; (b) Initial rates of GPx-like activities of CuNCs and various controls; (c) SOD-like activities of CuNCs (inset: $O_2$ generation rate); and (d) Comparison of catalytic activity of CuNCs with other metals.

(9) Non-Invasive Diagnostic of PD by TMHA $Cu^{2+}$ contents in human urine samples were measured using TMHA as probe. Remarkably, red fluorescence only appeared in the urine samples from PD patients. Considering its high specificity and simple operations, TMHA may open new opportunities in early diagnosis and risk assessment for PD.

Figure 9:
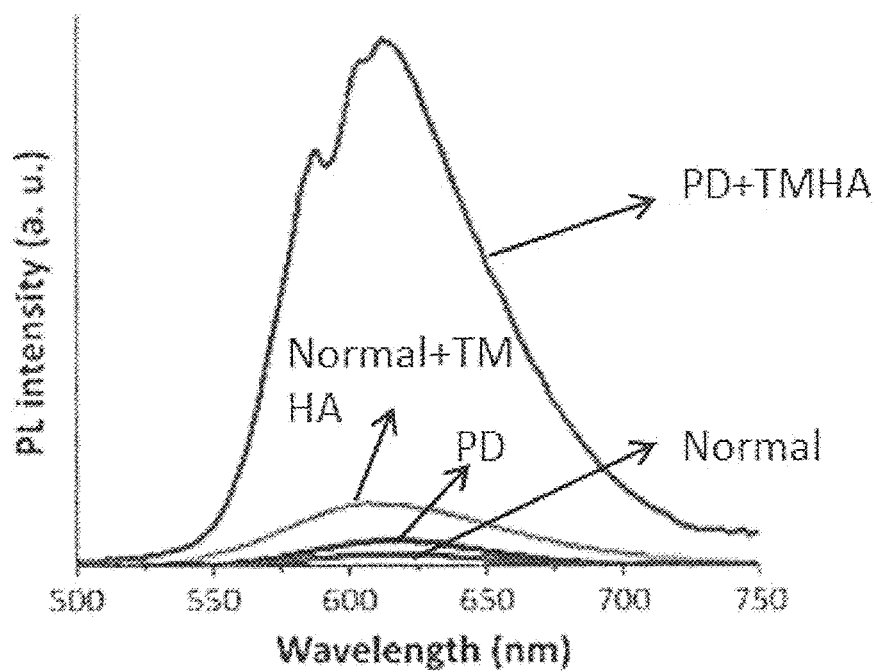
FIG. 9 provides graphs showing detection of urine $Cu^{2+}$ for early diagnosis of PD.

Referring now to FIG. 9, there is provided graphs showing detection of urine $Cu^{2+}$ for early diagnosis of PD.

(10) In Vitro Cell Experiments

PC12 (a rat adrenal medulla pheochromocytoma cell line), SHSY-5Y (a human neuroblastoma cell line), and HEK293 (a human embryonic kidney cell line) cells were cultured in Dulbecco's modified eagle medium (DMEM) medium supplemented with 10% (v/v) fetal bovine serum, 2 mM L-glutamine, 100 U $mL^{-1}$ penicillin, 100 µg $mL^{-1}$ streptomycin at 37° C. and 5% $CO_2$.

Methyl thiazolyl tetrazolium (MTT) assay was performed to measure in vitro cytotoxicity of TMHA by measuring cell viability. For the MTT assay, SHSY-5Y cells were seeded in 96-well plates at a density of 5000 viable cells per well and incubated for 24 h at 37° C. and 5% $CO_2$ to allow cell attachment. Then, the cells were incubated with blank TMHA solution (no $Cu^{2+}$ addition) at indicated concentrations. The cells were subsequently incubated for 24 h at 37° C. and 5% $CO_2$. After that the medium was replaced with fresh DMEM containing 5 mg $mL^{-1}$ MTT, the cells were incubated for an additional 4 h. After the removal of the MTT solution, the purple formazan crystals were dissolved with DMSO, and the absorbance was monitored at 570 nm on a micro-plate reader (FL600, Bio-Tek). The results were expressed as the mean values of three measurements. The same processes were performed to measure the in vitro cytotoxicity of pure THMA against HEK 293 cells and PC12 cells. TMHA was nontoxic at dosage high as 500 µg $mL^{-1}$.

We then investigated the cytoprotective property of TMHA in experimental cell model of PD phenotype. The model was generated via treating the rat adrenal pheochromocytoma cell (PC12) with $MPP^+$ (1-methyl-4-phenylpyridinium), an active metabolite of MPTP (1-methyl-4-phenyl-1,2,3,6-tetrahydropyridine).

1-methyl-4-phenyl-1,2,3,6-tetrahydropyridine (MPTP) is a neurotoxin. It is not toxic per se, but after it enters the brain, this neurotoxin is metabolized into the compound 1-methyl-4-phenylpyridine ($MPP^+$). $MPP^+$ can destroy DA-ergic neurons in the substantia nigra. At the same time, $MPP^+$ can interfere with NADH dehydrogenase, an important substance in the respiratory chain of mitochondrial metabolism, thus causes cell death and accumulation of free radicals. The mass death of DA-ergic neurons caused by this process severely affects motion control by the cerebral cortex, resulting in similar symptoms of PD. Therefore, MPTP and $MPP^+$ are widely used in the establishment of PD-related animal and cell models as well as the research and development of PD medications.

Figure 10A:
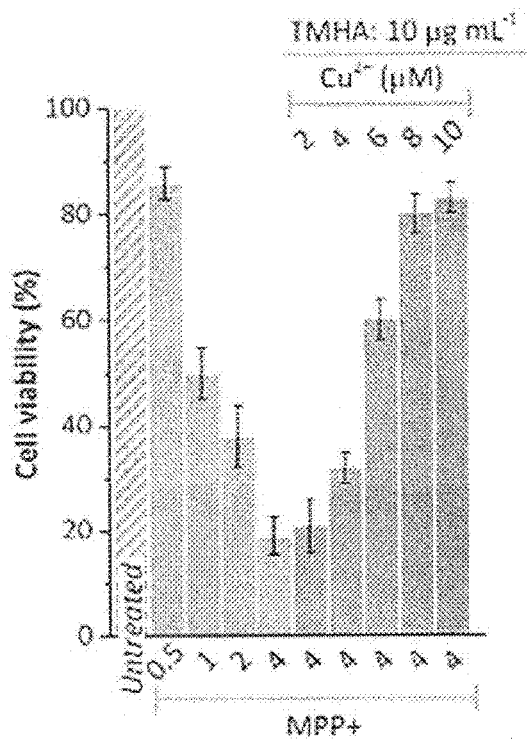
FIG. 10(a) provides bar graphs showing the data of cell viability (*** p<0.001)

PC12 cells were cultured in 6-well plates in the absence or presence of $Cu^{2+}$ and THMA. Various concentrations of $MPP^+$ (0.5-4 mM) was then added. The relative viability of cells was also determined by MTT assays. 4 mM $MPP^+$ triggered severe cytotoxicity of PC12 cells (i.e. only less than 20% cell viability). Excitingly, 4 mM $MPP^+$ triggered cytotoxicity was fully reversed by 8 µM $Cu^{2+}$ and 10 µg $ml^{-1}$ TMHA (i.e. more than 80% cell viability). The data of cell viability are shown in FIG. 10(a) (*** p<0.001).

Figures 10B, 10C:
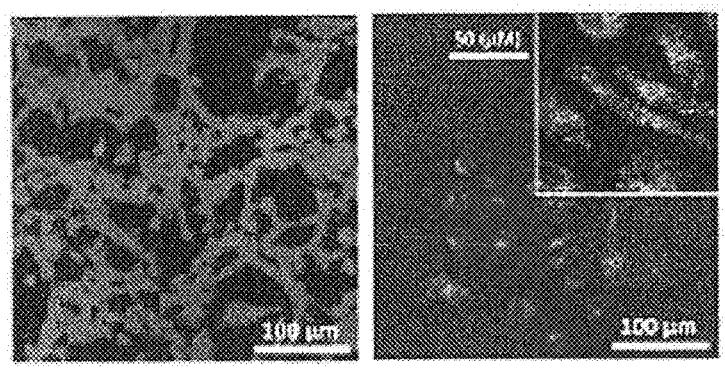
FIG. 10(b) shows dead (red) cells stained by PI dye, where the cells were treated with 4 mM $MPP^+$, 2 μM $Cu^{2+}$ and 10 μg $ml^{-1}$ TMHA.
FIG. 10(c) shows viable (green) cells stained by calcein-AM, where the cells were treated with 4 mM $MPP^+$, 10 μM $Cu^{2+}$ and 10 μg $ml^{-1}$ TMHA.

The cellular morphological alterations were acquired using confocal laser scanning microscopy (CLSM). For the observation of viable and dead cells on CLSM, 3',6'-Di(O-acetyl)-4',5'-bis[N,N-bis(carboxymethyl)aminomethyl]fluorescein (i.e. tetraacetoxymethyl ester (calcein-AM) was applied to stain the viable cells as green fluorescence ($\lambda_{ex}$=490 nm, $\lambda_{em}$=515 nm) and propidium iodide (PI) was employed to stain dead cells as red fluorescence ($\lambda_{ex}$=535 nm, $\lambda_{em}$=617 nm). Specifically, 0.1 mL of calcein-AM solution (20 mM) and 0.1 mL of PI solution (20 mM) were both added after the removal of culture medium. After 10 min of incubation, the two staining solutions were quickly removed, and the cells were rinsed by PBS twice. The obtained cells could be subsequently visualized by CLSM. FIG. 10(b) shows the dead (red) cells stained by PI dye, where the cells were treated with 4 mM $MPP^+$, 2 µM $Cu^{2+}$ and 10 µg $ml^{-1}$ TMHA; FIG. 10(c) shows viable (green) cells stained by calcein-AM, where the cells were treated with 4 mM $MPP^+$, 10 µM $Cu^{2+}$ and 10 µg $ml^{-1}$ TMHA.

Figure 11A:
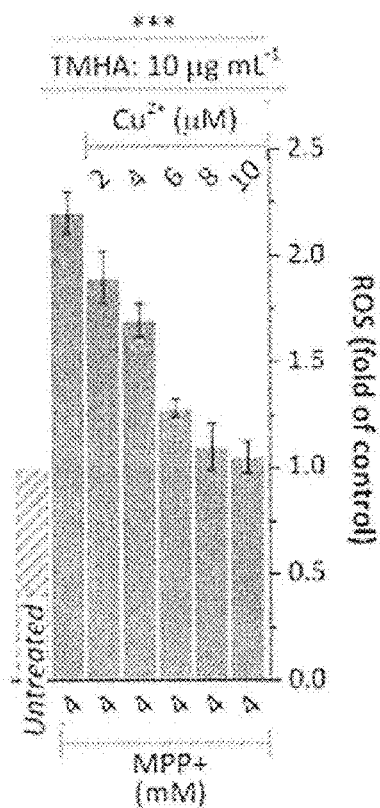
FIG. 11(a) provides bar graphs showing the data of the intracellular ROS levels, *** p<0.001.

In order to directly observe reactive oxygen species (ROS) using CLSM, PC12 cells were first seeded in a CLSM-exclusive culture disk and allowed to adhere overnight at 37° C. under 5% $CO_2$ gas. After incubation with 1 mL of 2',7'-dichlorofluorescein diacetate (DCFH-DA) for about 20 min, the culture solutions were replaced by fresh media (pH=7.4) containing the following substances: (a) 4 mM of $MPP^+$ as control, (b) 4 mM of $MPP^+$, 10 of µg $mL^{-1}$ TMHA, (c) 4 mM of $MPP^+$, 10 µM of $Cu^{2+}$, (d) 4 mM of $MPP^+$, 10 mg $mL^{-1}$ of TMHA, 2 µM of $Cu^{2+}$, (e) 4 mM of $MPP^+$, 10 µg $mL^{-1}$ of TMHA, 4 µM of $Cu_{2+}$; (f) 4 mM of $MPP^+$, 10 µg $mL^{-1}$ of TMHA, 6 µM of $Cu^{2+}$, (g) 4 mM of $MPP^+$, 10 µg $mL^{-1}$ of TMHA, 8 µM of $Cu^{2+}$, and (h) 4 mM of $MPP^+$, 10 µg $mL^{-1}$ of TMHA, 10 µM of $Cu^{2+}$, respectively. The cells were washed by fresh PBS twice after another incubation at 37° C. in 5% $CO_2$ for 30 min. The levels of intracellular ROS were evaluated by detecting the fluorescence of newly formed DCF ($\lambda_{ex}$=488 nm, $\lambda_{em}$=525 nm). The data of intracellular ROS levels are shown in FIG. 11(a); *** p<0.001.

Figures 11B, 11C:
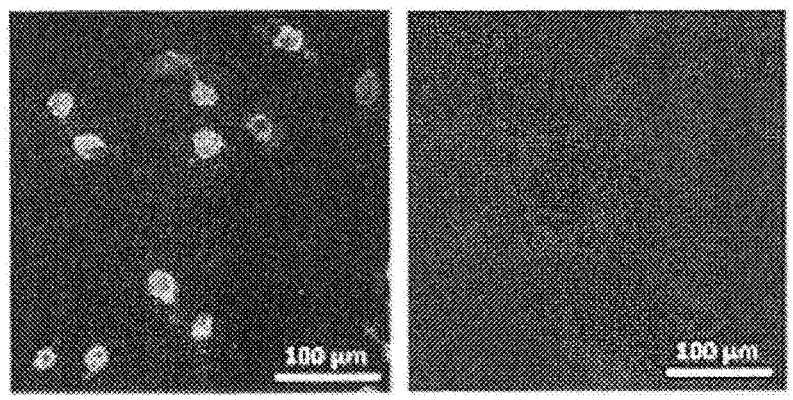
FIG. 11(b) shows a CLSM image of intracellular ROS in the cells that were treated with 4 mM of $MPP^+$, 10 of μg mL-1 TMHA, and stained using a specific fluorescence probe DCFH-DA.
FIG. 11(c) shows a CLSM image of intracellular ROS in the cells that were treated with 4 mM of $MPP^+$, 10 of μg $mL^{-1}$ TMHA, 10 μM of $Cu^{2+}$, and stained with DCFH-DA.

FIG. 11(b) shows a CLSM image of intracellular ROS in the cells that were treated with 4 mM of $MPP^+$, 10 of µg $mL^{-1}$ TMHA, and stained by specific fluorescence probe DCFH-DA; FIG. 11(c) shows a CLSM image of intracellular ROS in the cells that were treated with 4 mM of $MPP^+$, 10 of µg $mL^{-1}$ TMHA, 10 µM of $Cu^{2+}$, and stained by specific fluorescence probe DCFH-DA. Obvious decline of ROS-specific fluorescent intensity demonstrated that TMHA was capable of scavenging intracellular elevated ROS efficiently. The characteristic 1:2:2:1 hydroxyl radical spin further demonstrated the reduction of intracellular ROS induced by TMHA treatment.

(11) In Vivo Protection Experiments

Generally, it is widely accepted that administrations of 1-methyl-4-phenyl-1,2,3,6-tetrahydropyridine (MPTP) can result in clinical symptoms of animals remarkably similar to sporadic PD in humans. Hence, for our experiments, we utilized MPTP to produce parkinsonian symptoms in animal models of PD. Briefly, the C57BL/6 mice were randomly divided into 7 groups (n=5 mice/group), i.e., blank Control (normal saline), high dose of TMHA (100 mg kg$^{-1}$), low dose of TMHA (50 mg kg$^{-1}$), high dose of MPTP (30 mg kg$^{-1}$), low dose of MPTP (10 mg kg$^{-1}$), MPTP+TMHA (30 mg kg$^{-1}$+10 mg kg$^{-1}$), and MPTP+TMIA (30 mg kg$^{-1}$+20 mg kg$^{-1}$). Specifically, for the model group, MPTP was given by continuous intraperitoneal injection for at least 4 days to generate the mouse model of PD. The blank control group and THMA group were treated with saline and THMA by ip injection, respectively. For the MPTP+TMHA groups, the TMHA (dosage: 10 or 20 mg kg$^{-1}$) was injected intraperitoneally 0.5 h in advance (once per day) and then MPTP of 30 mg kg$^{-1}$ was injected intraperitoneally for 7 days.

Figure 12A:
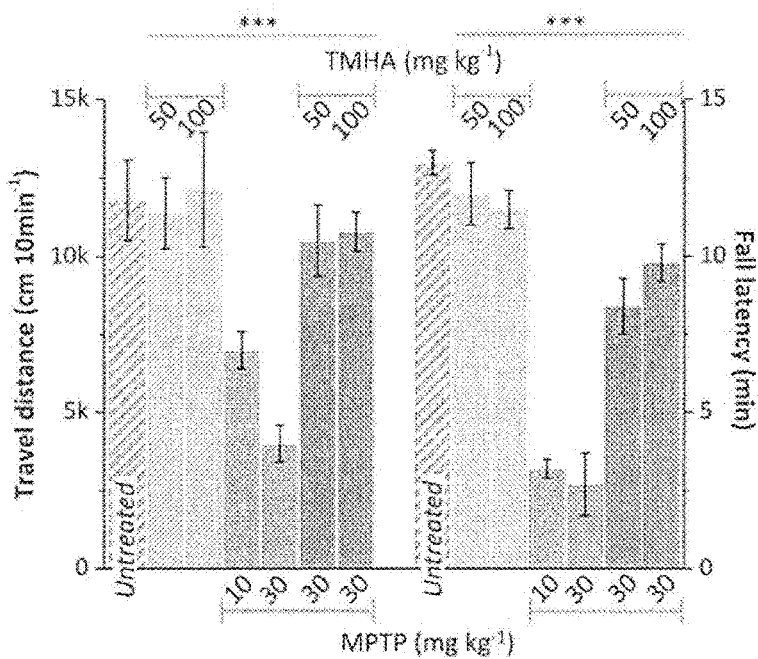
FIG. 12(a) shows the traveled distance and fall latency of mice with memory deficit, *** p<0.001.

The motor function was assessed via swim test. Each animal was placed in a circular pool with dimension of diameter 120 cm and height 80 cm. The depth of water (25° C.) was 60 cm. The traveled distance (cm 10 min$^{-1}$) and duration (sec) were both recorded at 10-min interval using a tracking system (Shanghai Jiliang Software Technology Co., Ltd.). The motor coordination and balance were measured using a rotarod (Ugo Basile). Mice were given three trials of 15 min on rotating rod that started at 10 rpm and accelerated to 22 rpm over 30 s. The inter-trial interval was 3 min. The time of falling from the rod was measured and averaged for each group. FIG. 12(a) shows the traveled distance and fall latency of mice with memory deficit; *** p<0.001. These data demonstrated that TMHA treatment could restore the cognitive activities of MPTP-treated animals.

Figure 12B:
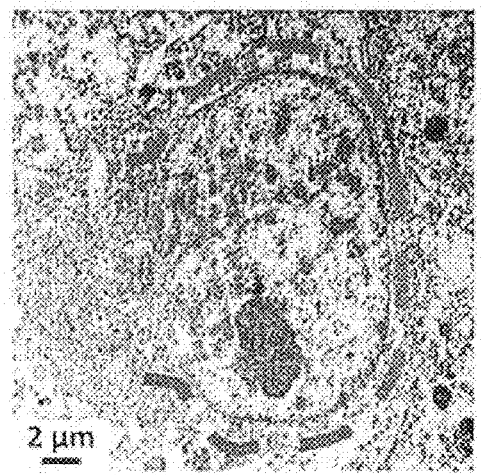
FIG. 12(b) shows a mitochondrion from an animal treated with high dose of MPTP (30 mg $kg^{-1}$), where as outlined via red line, the mitochondrion shows swollen, vacuolar shapes and severe cristae disruption.
Figure 12C:
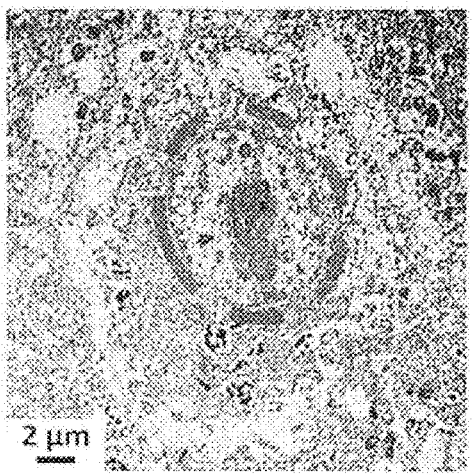
FIG. 12(c) shows a mitochondrion from an animal treated with MPTP (30 mg $kg^{-1}$)+TMHA (30 mg $kg^{-1}$), where as outlined via red line, the mitochondrion displays a normal morphology.

Variation in mitochondria morphology is an early and important sign of ROS-induced mitochondrial dysfunction. Here, we used TEM to visualize mitochondrial morphology alterations. Generally, brain tissues from C75BL/6 mice were sequentially fixed overnight in a mixture of cold 2.5% glutaraldehyde in 0.1 M PBS (pH 7.2) and 2% paraformaldehyde in 0.1 M phosphate buffer solution (pH 7.2) before being placed in epoxy resin. The embedded samples were loaded into capsules and polymerized at 38° C. for 9 h and then at 60° C. for 48 h. Thin sections were made using an ultramicrotome (RMC, USA) and collected on a copper grid. Appropriate areas for sections were cut at 100 nm thickness, and the sections were stained with saturated 4% uranyl acetate/4% lead citrate prior to TEM before examination with a transmission electron microscope (JEM-2100F) at 80 kV. FIG. 12(b) shows a mitochondrion from an animal treated with high dose of MPTP (30 mg kg$^{-1}$), where as outlined via red line, the mitochondrion shows swollen, vacuolar shapes and severe cristae disruption; in contrast, FIG. 12(c) shows a mitochondrion from an animal treated with MPTP (30 mg kg$^{-1}$)+TMHA (30 mg kg$^{-1}$), where as outlined via red line, the mitochondrion displays a normal morphology.

(12) α-Syn Aggregation Kinetics Experiments with Singular CuNCs with Different Ligands CuNCs modified with different ligands were prepared according to literatures. Thioflavin T (abbreviation: ThT) is a highly sensitive fluorescent marker used to identify the presence of amyloid. When ThT is incubated together with monomers of polypeptides or proteins, its fluorescence does not change substantially. When ThT encounters amyloid polypeptide or protein with a fiber structure, it will immediately adjacent to the amyloid polypeptides or proteins and its fluorescence intensity will increase exponentially. Therefore, ThT is widely used as a maker to monitor amyloidosis of peptides or proteins. This embodiment adopts ThT fluorescent labeling method to monitor the kinetics process of fibrosis aggregation of α-syn in the presence of CuNCs. The specific experiment method is as follows:

Pretreatment of α-syn monomers: Dissolve freeze-dried α-syn powder (Bachem Corp.) in HFIP to obtain a 1 g/L α-syn solution. Incubate it at room temperature for 2-4 h after scaling, then use high-purity nitrogen to blow HFIP dry at an appropriate flow rate in a fume cupboard, dissolve the dried α-syn in 200 μL of DMSO, seal the solution, keep it in a −20° C. refrigerator for future use, for at most one week. Before use, dilute the α-syn DMSO solution with profuse phosphate buffer solution (PBS, 10 mM, pH=7.4) to 20 μM, to obtain a α-syn PBS solution. All the α-syn PBS solutions in the experiment are prepared just before use.

Sample preparation and detection: Add ligand modified CuNCs to α-syn PBS solution to reach final concentrations of 5 ppm and 35 μM for CuNCs and α-syn, respectively. Incubate the solution continuously in a 96-well plate at 37° C., monitor the fluorescence intensity by microplate reader every 10 minutes, and characterize the kinetics process of α-syn aggregation through the change of fluorescence intensity of ThT. The experimental group takes the ligand modified CuNCs. The ligand control group adopts ligand molecules not combined to CuNCs. The blank control group adopts α-syn only.

Figure 13:
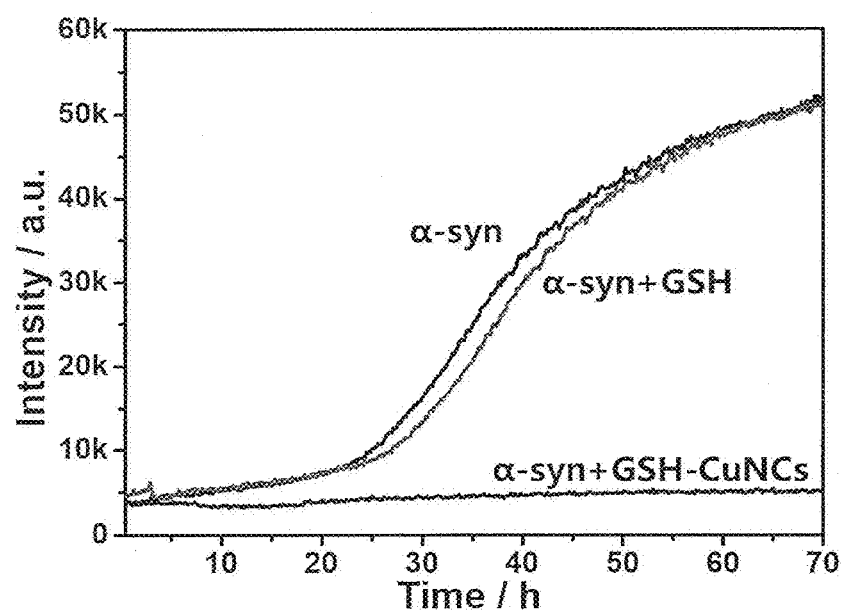
FIG. 13 provides graphs showing the effect of L-glutathione (GSH) modified CuNCs (GSH—CuNCs) on α-syn fibrosis kinetics.

Referring now to FIG. 13, there are provided graphs showing the effect of L-glutathione (GSH) modified CuNCs (GSH—CuNCs) on α-syn fibrosis kinetics. The results indicate that in the incubation process of 35 μM α-syn at 37° C., ThT-labeled fluorescence intensity increases rapidly from the 25$^{th}$ hour, demonstrating that α-syn aggregation and fibrosis happened. The result of the ligand control group indicates that using ligand GSH alone does not have an obvious effect on aggregation kinetics of α-syn. As for the experimental group with addition of CuNCs, ThT-labeled fluorescence intensity remains near the base line without any increase throughout the 70 hours of experiment, suggesting that GSH modified CuNCs can inhibit α-syn aggregation and fibrosis completely, and the effect is due to CuNCs, but not the GSH ligands.

In certain embodiments, CuNCs were modified with other ligands, e.g. including L(D)-cysteine, N-isobutyryl-L(D)-cysteine (L(D)-NIBC) and N-acetyl-L(D)-cysteine (L(D)-NAC), and the modified CuNCs are also studied using the same protocols. A similar phenomenon is also observed for CuNCs modified with different ligands, and the same conclusion can be made: these ligands per se cannot influence α-syn aggregation and fibrosis, while ligand-modified CuNCs can inhibit α-syn aggregation and fibrosis completely.

(13) MPP$^+$ Induced PD Cells (SH-sy5y) Model Experiment

The experiment uses cell viability obtained from the test result of CCK-8 method as an indicator, to reflect the resistance efficacy of ligand-modified CuNCs against the toxic effect of MPP$^+$ (a common-used neurotoxin) in SH-sy5y cell model of PD to demonstrate their neuroprotective effect on PD. Specific method:

1) Take SH-sy5y cells in the logarithmic growth phase. Dilute them with complete medium to form a cell suspension with a cell density of $5\times10^4$/mL. Plate 200 μl of the cell suspension into each well of a 96-well plate and cultivate in an environment of 37° C. and 5% $CO_2$ in an incubator. The sample is added after the cells are attached.

2) Add 100 μL of ligand-modified CuNCs samples or ligand-modified copper nanoparticles samples with different particle sizes, which are prepared using maintenance medium to make the final concentration being 0.1 ppm, 1 ppm, 5 ppm, 10 ppm and 20 ppm, respectively. After 2 hours of pretreatment with ligand-modified CuNCs, the different groups of cells were added with $MPP^+$ (final concentration is 1 mM). A blank control that did not contain SH-sy5y cells, a negative control group containing SH-sy5y cells but without CuNCs and $MPP^+$, a cell control group containing SH-sy5y cells and 1 mM $MPP^+$ only, a sample control group containing SH-sy5y cells and 100 ppm CuNCs but without $MPP^+$, and a ligand control group containing SH-sy5y cells and 1 mM $MPP^+$ and corresponding ligand molecules (final concentration is 20 ppm) were set. Then the cells were cultured at 37° C. for 24 h. After centrifugation to remove the culture medium, 100 μL maintenance medium containing 10% CCK-8 were added to each well, and then incubate for 4 h. The absorbance of each well was then measured at 450 nm. The absorbance could reflect the pre-protective and curative effects of ligand-modified CuNCs against $MPP^+$ lesion.

Figure 14:
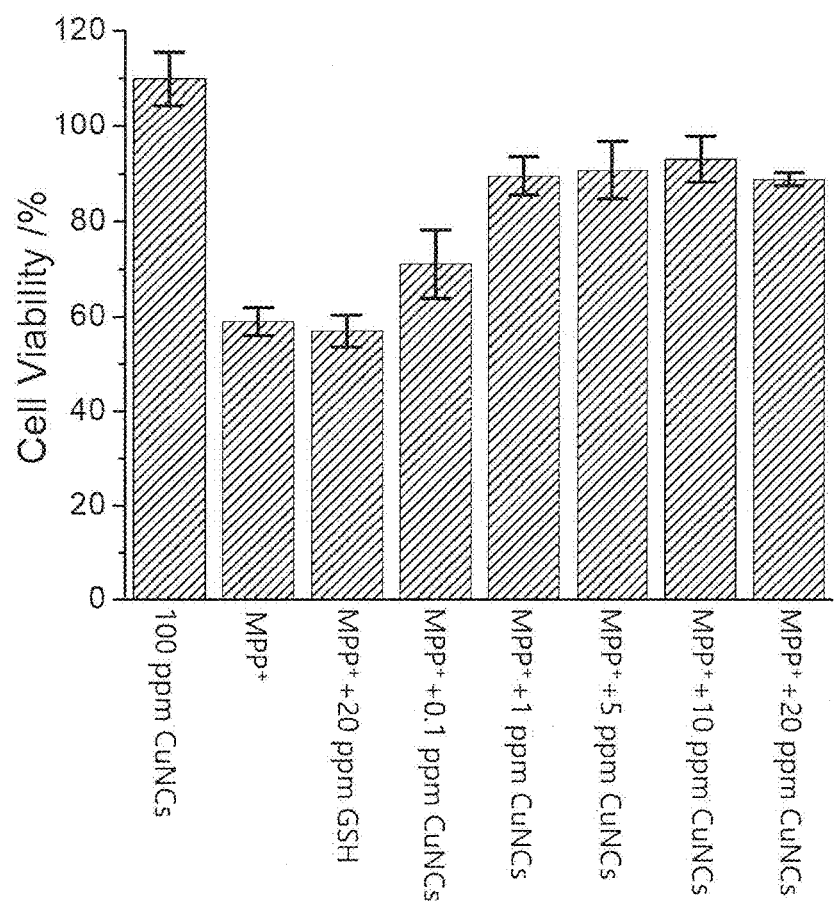
FIG. 14 provides bar graphs showing the effect of CuNCs on the cell viability of $MPP^+$-lesioned PD cell (SH-sy5y) model.
Figure 15A:
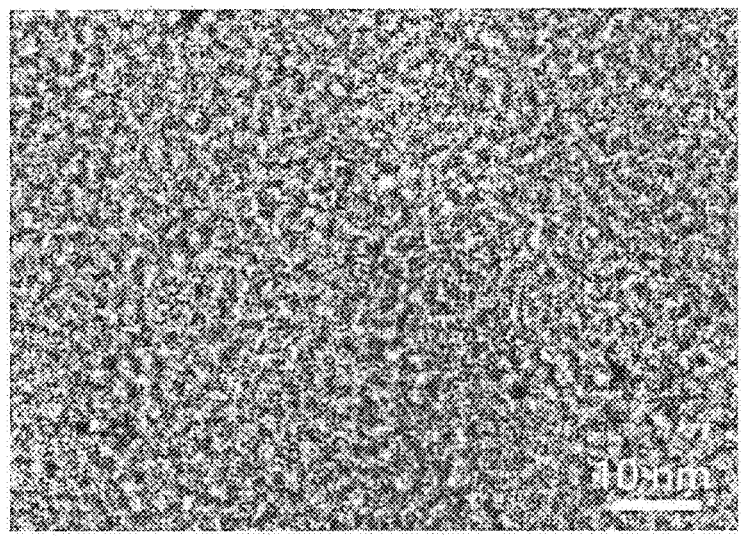
FIG. 15 shows characterization data of CuNCs. (A) A typical transmission electron microscopic (TEM) image of CuNCs. (B) Size distribution of CuNCs calculated from TEM images. (C) X-ray photoelectron spectroscopy (XPS) spectrum of $2p_{3/2}$ and $2p_{1/2}$ electrons of Cu(0) in CuNCs. (D) Comparison between Fourier transform infrared (FT-IR) spectroscopies of GSH modified CuNCs (upper) and GSH (lower). (E) Fluorescent excitation (left) and emission spectra (right) of CuNCs.
Figure 15B:
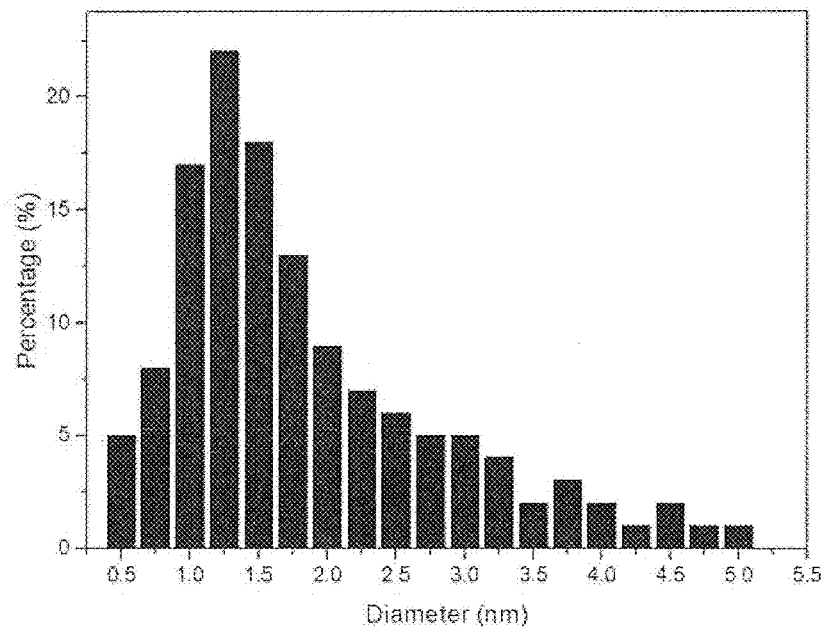
Figure 15C:
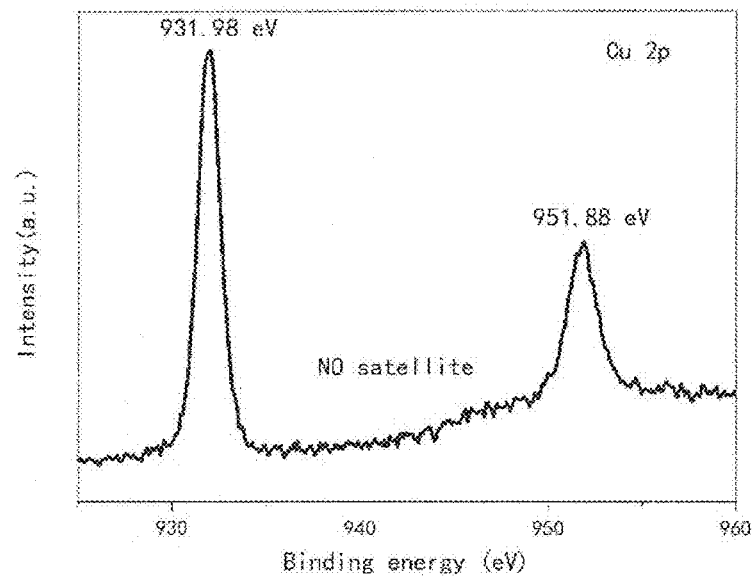
Figure 15D:
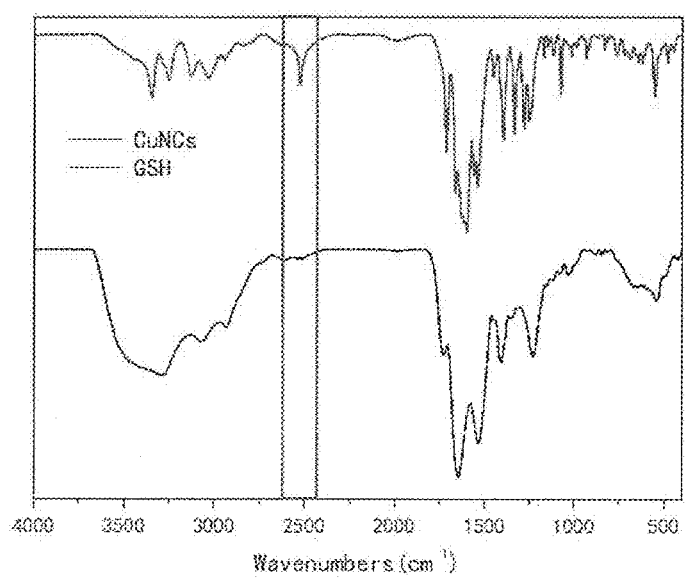
Figure 15E:
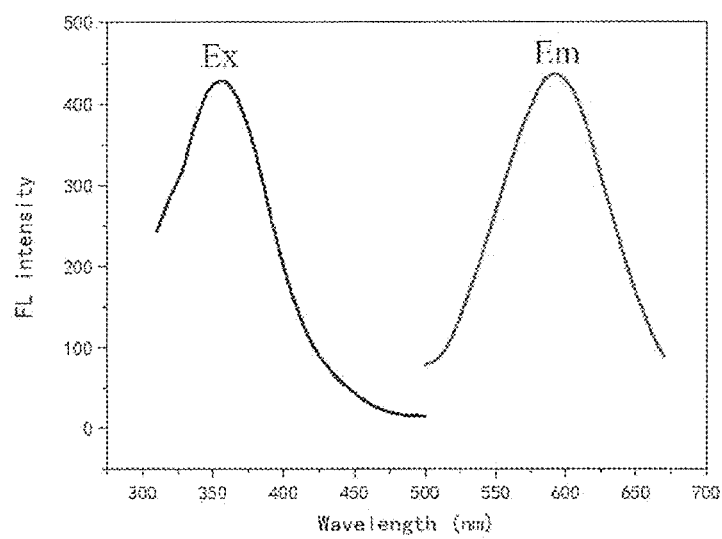

Referring now to FIG. 14, there are provided bar graphs showing the effect of CuNCs on the cell viability of $MPP^+$-lesioned PD cell (SH-sy5y) model. The results indicate that after 24 h of cultivation, the cell viability of the sample control group added with 100 ppm CuNCs, but not treated with $MPP^+$ increases to 110.0±6.2% relative to the blank control group (set as 100%) ($P<0.01$), suggesting that CuNCs are nontoxic. The cell viability of the model control group added with 1 mM $MPP^+$ but without CuNCs decreases to 58.9±5.4% ($P<0.01$, v.s. the blank control group), the cell viability of the ligand control group is 56.9±3.4% ($P<0.01$, v.s. the blank control group), suggesting that ligand alone does not raise the viability of $MPP^+$ lesioned cells. While the cell viability of the administration groups which were added with 0.1 ppm, 1 ppm, 5 ppm, 10 ppm and 20 ppm of CuNCs increases to 70.9±7.1% ($P<0.001$, v.s. the model control group), 89.3±4.1% ($P<0.001$, v.s. the model control group), 90.5±6.1% ($P<0.001$, v.s. the model control group), 92.8±4.8% ($P<0.001$, v.s. the model control group) and 88.5±1.4% ($P<0.001$, v.s. the model control group). The results suggest that the ligand-modified CuNCs provided by the present invention have a significant protective effect on nerve cells in PD, and this effect is due to CuNCs other than the ligand.

The same steps are also adopted to carry out the experiments for the CuNCs modified with other ligands, e.g. L(D)-cysteine, N-isobutyryl-L(D)-cysteine (L(D)-NIBC) and N-acetyl-L(D)-cysteine (L(D)-NAC). The effect is similar and will not be described in detail.

(14) Characterization of CuNCs

CuNCs modified with one or more ligands were synthesized. The ligands include thymine, L(D)-cysteine and other cysteine derivatives such as N-isobutyryl-L-cysteine (L-NIBC), N-isobutyryl-D-cysteine (D-NIBC), N-acetyl-L-cysteine and N-acetyl-D-cysteine, cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol and dodecyl mercaptane.

The following are characterization data of GSH modified CuNCs are shown in following as an example.

1) Observation of the Morphology by Transmission Electron Microscope (TEM)

The test powders (GSH modified CuNCs sample) were dissolved in ultrapure water to 2 mg/L as samples, and then test samples were prepared by hanging drop method. The specific method: 5 μL of the samples were dripped on the copper mesh, volatized naturally till the water drop disappeared, and then observe the morphology of the samples by JEM-2100F STEM/EDS field emission high-resolution TEM.

Panel A and panel B of FIG. 15 show a typical SEM image of GSH modified CuNCs, and their size distribution was calculated from different TEM images. It indicates that CuNCs are well-dispersed and their sizes lie in a range of 0.5-5.0 nm.

2) X-Ray Photoelectron Spectroscopy

The X-ray photoelectron spectroscopy (XPS) spectra was measured on a ESCALAB 250Xi X-ray photoelectron spectrometer. A double-sided conductive adhesive (3 mm×3 mm) was attached to the aluminum foil, the test powder was evenly spread on the double-sided tape and covered with a layer of aluminum foil. The sample was kept under a pressure of 8 MPa for one minute. Remove the residual powder on the surface and then the center sample (1 mm×1 mm) was cut out for XPS testing.

Panel C of FIG. 15 is the XPS spectrum of Cu element in CuNCs. Two peaks appear at 931.98 and 951.88 eV, which can be ascribed to the binding energies of the $2p_{3/2}$ and $2p_{1/2}$ electrons of Cu, respectively. The absence of Cu $2p_{3/2}$ satellite peak around 942.0 eV confirms that the Cu(II) electrons are not present. As the binding energy of Cu(0) is only 0.1 eV away from that of Cu(I), it is not possible to exclude the formation of Cu(I), and the valence state of Cu in the obtained GSH modified CuNCs most likely lies between 0 and +1.

3) Fourier Transform Infrared (FT-IR) Spectroscopy

The FT-IR spectra was tested on the PerkinElmer LS 55 fluorescence spectrometer. The test powder was dissolved in ultrapure water, and measured at room temperature. The scanning range was 200-800 nm, the sample cell was a standard quartz cuvette with an optical path of 1 cm.

Panel D of FIG. 15 shows a comparison between FT-IR spectroscopies of GSH modified CuNCs (upper) and GSH (lower). GSH exhibits a number of characteristic IR bands, i.e., $COOH^-$ (1,390 and 1,500 $cm^{-1}$), the N—H stretch (3,410 $cm^{-1}$), and the N—H bending (1,610 $cm^{-1}$) of $NH_2$ group. The peak observed at 2,503 $cm^{-1}$ can be assigned to the S—H stretching vibrational mode. Corresponding characteristic IR bands can all be found for GSH modified CuNCs, except for the S—H stretching vibration band (2,503 $cm^{-1}$). It suggests the cleavage of the S—H bond and the binding of the GSH molecules to the surface of CuNCs through the formation of Cu—S bond.

4) Fluorescence Spectroscopy

The test powder was dissolved in ultrapure water, and measured by fluorescence spectroscopy at room temperature.

As shown in the panel E of FIG. 15, the CuNCs exhibit red emission with a peak at 595 nm and a corresponding full width at half maximum (FWHM) of approximately 80 nm under the excitation peak at 365 nm. It is worth noting that the FL intensity of the CuNCs will be significant improved when the ethanol was added to the solution due to the aggregation induced emission enhancement. In addition, the large stokes shift (230 nm) indicated good prospects for fluorescent probes and bioimaging.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

REFERENCES

Dudzik C G, et al. Coordination features and affinity of the $Cu^{2+}$ site in the α-synuclein protein of Parkinson's disease. Biochemistry. 2011; 50:1771-7

Giampietro R, et al. The Pivotal Role of Copper in Neurodegeneration: A New Strategy for the Therapy of Neurodegenerative Disorders. *Mol. Pharmaceutics* 2018; 15: 808-820

Jin R, et al. Atomically Precise Colloidal Metal Nanoclusters and Nanoparticles: Fundamentals and Opportunities, *Chem. Rev.,* 2016, 116, 10346-10413

Kozlowski H, et al., Copper, zinc and iron in neurodegenerative diseases (Alzheimer's, Parkinson's and prion diseases). *Coordination Chemistry Reviews* 2012; 256: 2129-2141

Liu X, et al. Atomically Precise Copper Nanoclusters and Their Applications, *Coord. Chem. Rev.,* 2018, 359, 112-126

Manna U, et al. Layer-by-layer self-assembly of modified hyaluronic acid/chitosan based on hydrogen bonding. Biomacromolecules. 2009; 10: 2632-9

McLeary F A, et al. Dexamethasone Inhibits Copper-Induced Alpha-Synuclein Aggregation by a Metallothionein-Dependent Mechanism. Neurotox Res. 2018; 33: 229-238

Tristan-Lopez L, et al. Copper and Copper Proteins in Parkinson's Disease. *Oxidative Medicine and Cellular Longevity.* 2014; Article ID 147251

Yang D, et al. Poly(thymine)-Templated Selective Formation of Copper Nanoparticles for Alkaline Phosphatase Analysis Aided by Alkyne-Azide Cycloaddition "Click" Reaction. *ACS Appl. Nano Mater.* 2018; 1: 168-174

Yao Q, et al. Toward Total Synthesis of Thiolate-Protected Metal Nanoclusters, *Acc. Chem. Res.;* 2018; 51; 1338-1348

The invention claimed is:

1. Copper nanoclusters (CuNCs) modified with one or more ligands, wherein the ligand-modified CuNCs have a diameter in the range of 0.5-5 nm;

wherein the one or more ligands is (are) selected from the group consisting of, N-isobutyryl-L-cysteine (L-NIBC), N-isobutyryl-D-cysteine (D-NIBC), N-acetyl-D-cysteine, L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), glycine-L-serine-L-cysteine-L-arginine tetrapeptide (GSCR) and glycine-L-cysteine-L-serine-L-arginine tetrapeptide (GCSR), and 1-[(2S)-2-methyl-3-thiol-1-oxopropyl]-L-proline.

2. The CuNCs of claim 1, wherein the ligand-modified CuNCs have a diameter in the range of 0.5-3 nm.

3. The CuNCs of claim 1, wherein the ligand-modified CuNCs have a diameter in the range of 0.5-2.5 nm.

4. Thymine-modified hyaluronic acid (TMHA), wherein the TMHA is represented by formula I:

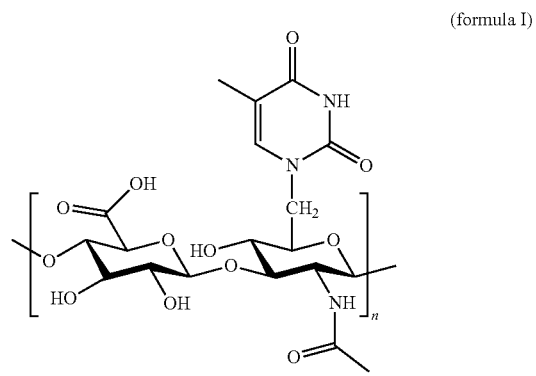

(formula I)

wherein the degree of substitution of thymine in the HA is in a range of 1-50%, and wherein n for GlcA-GlcNAc repeats is an integer, from 10 to 10,000.

5. The TMHA of claim 4, wherein the degree of substitution of thymine in the HA is in a range of 4-30%.

6. The TMHA of claim 4, wherein the degree of substitution of thymine in the HA is in a range of 5-20%.

7. The TMHA of claim 4, wherein the degree of substitution of thymine in the HA is in a range of 7-16%.

8. The TMHA of claim 4, wherein the degree of substitution of thymine in the HA is in a range of 8-15%.

9. The TMHA of claim 4, wherein the n is from 10 to 1,000.

10. The TMHA of claim 4, wherein the n is from 10 to 100.

11. Poly(copper nanoclusters) (PCuNCs), comprising:

thymine-modified hyaluronic acid (TMHA); and a plurality of copper nanoclusters (CuNCs);

wherein the CuNCs are disposed along the TMHA to form the PCuNCs;

wherein the TMHA is represented by formula I:
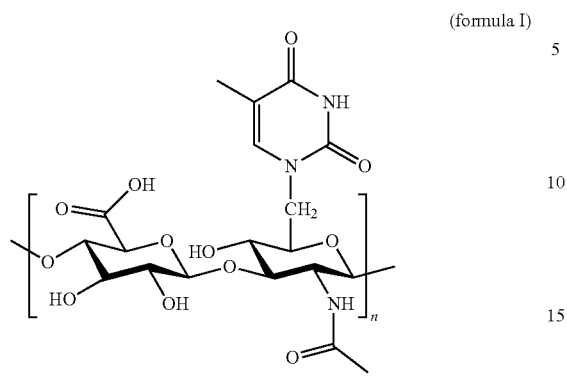
(formula I)
wherein the degree of substitution of thymine in the HA is in a range of 1-50%, and wherein n for GlcA-GlcNAc repeats is an integer, from 10 to 10,000.
12. The PCuNCs of claim 11, wherein the molar ratio between Cu and TMHA is 10:1 to 500:1.
13. The PCuNCs of claim 11, wherein the plurality of CuNCs are with diameters of 0.5-3 nm.
* * * * *